(12) United States Patent
Barnes et al.

(10) Patent No.: US 11,164,316 B2
(45) Date of Patent: Nov. 2, 2021

(54) IMAGE PROCESSING SYSTEMS AND METHODS FOR DISPLAYING MULTIPLE IMAGES OF A BIOLOGICAL SPECIMEN

(71) Applicants: Ventana Medical Systems, Inc., Tucson, AZ (US); Providence Health & Services—Oregon, Portland, OR (US)

(72) Inventors: Michael Barnes, Oro Valley, AZ (US); Carlo Bifulco, Portland, OR (US); Christophe Chefd'hotel, San Jose, CA (US); Ting Chen, Sunnyvale, CA (US); Alisa Tubbs, Phoenix, AZ (US)

(73) Assignee: VENTANA MEDICAL SYSTEMS, INC., Tucson, AZ (US)

( * ) Notice: Subject to any disclaimer, the term of this patent is extended or adjusted under 35 U.S.C. 154(b) by 0 days.

(21) Appl. No.: 16/724,227

(22) Filed: Dec. 21, 2019

(65) Prior Publication Data

US 2020/0143542 A1    May 7, 2020

Related U.S. Application Data

(60) Division of application No. 15/910,972, filed on Mar. 2, 2018, now Pat. No. 10,552,960, which is a
(Continued)

(51) Int. Cl.
*G06T 3/00* (2006.01)
*G06T 7/00* (2017.01)
(Continued)

(52) U.S. Cl.
CPC ............ *G06T 7/0016* (2013.01); *G06K 9/469* (2013.01); *G06T 3/0006* (2013.01);
(Continued)

(58) Field of Classification Search
CPC . G16B 45/00; G06F 3/04845; G06F 3/04883; G06K 9/469; G06T 3/0006;
(Continued)

(56) References Cited

U.S. PATENT DOCUMENTS 10,552,960 B2    2/2020   Barnes et al.
2009/0141959 A1*  6/2009   Can .................... G01N 21/6428
                                                      382/133
(Continued)

FOREIGN PATENT DOCUMENTS

EP      2634749 A2    9/2013
EP      2639765 A2    9/2013
WO   2014/089499 A1   6/2014

OTHER PUBLICATIONS

International Search Report and Written Opinion dated Mar. 9, 2017 in related foreign application No. PCT/EP2016/070105, all pgs.
(Continued)

*Primary Examiner* — Diane M Wills
(74) *Attorney, Agent, or Firm* — Kilpatrick Townsend & Stockton LLP

(57) ABSTRACT

A system and method of displaying of multiple simultaneous views of a same region of a biological tissue sample. Logical instructions are executed by a processor to perform operations such as receiving a plurality of images of the biological tissue sample, converting the plurality of images to a common reference frame based on the individual metadata of each image, and arranging the plurality of images into a display pattern for simultaneous viewing of different aspects of the imaged biological tissue sample on a display screen. The plurality of images is produced by preprocessing images of the biological tissue sample. Each image shows a view mode of a same region of the biological tissue sample, and each image contains metadata that describe spatial orienta-
(Continued)

tion, such as the translation, rotation, and magnification, of the image to bring the plurality of images to a common view.

17 Claims, 26 Drawing Sheets

Related U.S. Application Data continuation of application No. PCT/EP2016/070105, filed on Aug. 25, 2016.

(60) Provisional application No. 62/213,487, filed on Sep. 2, 2015.

(51) Int. Cl.

| | | |
|---|---|---|
| *G06T 11/60* | (2006.01) | |
| *G06T 7/11* | (2017.01) | |
| *G06K 9/46* | (2006.01) | |
| *G06T 11/00* | (2006.01) | |
| *G16B 45/00* | (2019.01) | |
| *G06F 3/0481* | (2013.01) | |
| *G06F 3/0488* | (2013.01) | |

(52) U.S. Cl.
CPC .............. *G06T 7/0012* (2013.01); *G06T 7/11* (2017.01); *G06T 11/005* (2013.01); *G06T 11/60* (2013.01); *G06F 3/04817* (2013.01); *G06F 3/04883* (2013.01); *G06T 2200/24* (2013.01); *G06T 2207/20192* (2013.01); *G16B 45/00* (2019.02)

(58) Field of Classification Search
CPC ....... G06T 3/0068; G06T 3/40; G06T 7/0012; G06T 7/0016; G06T 7/11; G06T 7/30; G06T 7/32; G06T 7/38; G06T 11/60; G06T 2200/24; G06T 2207/30004–30104; G06T 2207/30204

See application file for complete search history.

(56) References Cited

U.S. PATENT DOCUMENTS

| | | | |
|---|---|---|---|
| 2009/0245610 A1* | 10/2009 | Can | G01N 1/312 |
| | | | 382/133 |
| 2012/0069049 A1 | 3/2012 | Howe et al. | |
| 2013/0170728 A1* | 7/2013 | Sarachan | G06T 7/11 |
| | | | 382/133 |
| 2013/0287283 A1* | 10/2013 | Kamath | G06K 9/0014 |
| | | | 382/133 |
| 2015/0301732 A1* | 10/2015 | Henderson | G06F 3/04842 |
| | | | 715/769 |
| 2015/0310652 A1* | 10/2015 | Dobson | G06F 3/04845 |
| | | | 345/629 |

OTHER PUBLICATIONS

International Preliminary Report on Patentability dated Mar. 6, 2018 in related foreign application No. PCT/EP2016/070105, all pgs.
Non-Final Office Action dated May 17, 2019 in related U.S. Appl. No. 15/910,972, all pgs.
Notice of Allowance dated Sep. 27, 2019 in related U.S. Appl. No. 15/910,972, all pgs.

* cited by examiner

Candidate FOVs for Marker 1

+

Candidate FOVs for Marker 2

+

. . .

Candidate FOVs for Marker N

=

Final FOVs

Fig. 5A

Candidate FOVs for Marker 1

Candidate FOVs for Marker 2

. . .

Candidate FOVs for Marker N

+ = Final FOVs

Fig. 5B

IMAGE PROCESSING SYSTEMS AND METHODS FOR DISPLAYING MULTIPLE IMAGES OF A BIOLOGICAL SPECIMEN

CROSS-REFERENCE TO RELATED APPLICATIONS

This patent application is a divisional application of U.S. patent application Ser. No. 15/910,972 filed Mar. 2, 2018 which is a continuation of International Patent Application No. PCT/EP2016/070105 filed Aug. 25, 2016, which claims priority to and the benefit of U.S. Provisional Patent Application No. 62/213,487, filed Sep. 2, 2015, the contents of which are incorporated by reference herein in their entirety for all purposes.

APPLICATIONS BACKGROUND OF THE SUBJECT DISCLOSURE

Field of the Subject Disclosure

The present subject disclosure relates to imaging for medical diagnosis. More particularly, the present subject disclosure relates to the display and transformation of field of view (FOV) images in unison.

Background of the Subject Disclosure

In the analysis of biological specimens such as tissue sections, blood, cell cultures and the like, biological specimens are stained with one or more combinations of stains, and the resulting assay is viewed or imaged for further analysis. Observing the assay enables a variety of processes, including diagnosis of disease, assessment of response to treatment, and development of new drugs to fight disease. An assay includes one or more stains conjugated to an antibody that binds to protein, protein fragments, or other objects of interest in the specimen, hereinafter referred to as targets or target objects. The antibodies or other compounds that bind a target in the specimen to a stain are referred to as biomarkers in this subject disclosure. Some biomarkers have a fixed relationship to a stain (e.g., the often used counterstain hematoxylin), whereas for other biomarkers, a choice of stain may be used to develop and create a new assay. Subsequent to staining, the assay may be imaged for further analysis of the contents of the tissue specimen. An image of an entire slide is typically referred to as a whole-slide image, or simply whole-slide.

Typically, in immunoscore computations, a scientist uses a multiplex assay that involves staining one piece of tissue or a simplex assay that involves staining adjacent serial tissue sections to detect or quantify, for example, multiple proteins or nucleic acids etc. in the same tissue block. With the stained slides available, the immunological data, for instance, the type, density and location of the immune cells, can be estimated from the tumor tissue samples. It has been reported that this data can be used to predict the patient survival of colorectal cancer and demonstrates important prognostic role.

In the traditional workflow for immunoscore computation, the expert reader such as a pathologist or biologist selects the representative fields of view (FOVs) or regions of interest (ROIs) manually, as the initial step, by reviewing the slide under a microscope or reading an image of a slide, which has been scanned/digitized, on a display. When the tissue slide is scanned, the scanned image is viewed by independent readers and the FOVs are manually marked based on the readers' personal preferences. After selecting the FOVs, the computer produces counts of immune cells via an automatic algorithm in each FOV, or a pathologist/reader manually counts the immune cells within the selected FOVs. Manual selection of the FOVs and counting is highly subjective and biased to the readers, as different readers may select different FOVs to count. Hence, an immunoscore study is no longer reproducible. By automating the selection of the fields of view, a uniform method is applied reducing the subjectivity of independent readers. Use of low-resolution images to perform the FOV selection furthermore improves computational efficiency, allowing the analyst to rapidly proceed to analysis of the tissue regions.

It is often the case that any single view of a tissue sample may lead to several possible diagnoses of disease state. A tedious examination of several different views must rely on the memory of the expert reader in order to narrow the focus on any particular diagnosis.

Prior art includes, for example, US2003/0210262 by Graham et al. that generally teaches displaying at least two views of the same region on a microscope slide adjacent to each other, where the views offer differing illumination conditions, and the viewing device offers similar rectilinear translations.

Lastly, US2012/0320094 by Ruddle et al. generally teaches displaying at least two microscope slide images of the same region, adjacent to each other on a viewing screen, at different magnifications.

The automatic identification of FOVs is disclosed in U.S. 62/005,222, and PCT/EP2015/062015 the entirety being incorporated by reference herewith.

SUMMARY OF THE SUBJECT DISCLOSURE

The present invention provides an image processing method for displaying multiple images of a biological tissue region and a respective image processing system as claimed in the independent claims. Embodiments of the invention and further aspects of the invention are provided in the further dependent and independent claims.

A 'tissue sample' as understood herein is any biological sample obtained from a tissue region, such as a surgical biopsy specimen that is obtained from a human or animal body for anatomic pathology. The tissue sample may be a prostrate tissue sample, a breast tissue sample, a colon tissue sample or a tissue sample obtained from another organ or body region.

A 'multi-channel image' as understood herein encompasses a digital image obtained from a biological tissue sample in which different biological structures, such as nuclei and tissue structures, are simultaneously stained with specific fluorescent dyes, each of which fluoresces in a different spectral band thus constituting one of the channels of the multi-channel image. The biological tissue sample may be stained by a plurality of stains and/or by a stain and a counterstain, the later being also referred to as a "single marker image".

An 'unmixed image' as understood herein encompasses a grey-value or scalar image obtained for one channel of a multi-channel image. By unmixing a multi-channel image one unmixed image per channel is obtained.

A 'color channel' as understood herein is a channel of an image sensor. For example, the image sensor may have three color channels, such as red (R), green (G) and blue (B).

A 'heat map' as understood herein is a graphical representation of data where the individual values contained in a matrix are represented as colors.

'Thresholding' as understood herein encompasses the application of a predefined threshold or sorting of local maxima to provide a sorted list and selecting of a predetermined number of the local maxima from the top of the sorted list.

'Spatial low pass filtering' as understood herein encompasses a spatial filtering using a spatial filter that performs a low pass filtering operation on a neighborhood of image pixels, in particular a linear or non-linear operation. In particular, spatial low pass filtering may be performed by applying a convolutional filter. Spatial filtering is as such known from the prior art, (cf. Digital Image Processing, Third Edition, Rafael C. Gonzalez, Richard E. Woods, page 145, chapter 3.4.1).

'Local maximum filtering' as understood herein encompasses a filtering operation where a pixel is considered a local maximum if it is equal to the maximum value in a subimage area. Local maximum filtering can be implemented by applying a so called max filter, (cf. Digital Image Processing, Third Edition, Rafael C. Gonzalez, Richard E. Woods, page 326, chapter 5).

A 'field of view (FOV)' as understood herein encompasses an image portion that has a predetermined size and shape, such as a rectangular or circular shape.

In accordance with embodiments of the invention a tissue region of a cancer biopsy tissue sample is sliced into neighboring tissue slices. The tissue slices may be marked by single or multiple stains for the identification of respective biological features. A digital image is acquired from each of the marked tissue slices by means of an image sensor that has a number of color channels, such as an RGB image sensor.

An image registration algorithm is performed with respect to the acquired multiple digital images. Various suitable image registration algorithms that are as such known from the prior art can be used for performing the image registration, (cf. https://en.wikipedia.org/wiki/Image_registration and http://tango.andrew.cmu.edu/~gustavor/42431-intro-bioimagining/readings/ch8.pdf). In particular, an affine transformation can be utilized to perform the image registration.

The image registration algorithm generates a geometrical transformation that aligns corresponding points of the images. The geometrical transformation can be provided in the form of mappings, where each mapping maps the points of one of the images to corresponding points of another one of the images.

The images are aligned in accordance with the image registration. In other words, the geometrical transformations that are generated by the image registration algorithm are applied to the images for aligning the images in order to display the aligned images on a display in a two-dimensional plane. As a result the display shows the multiple images after registration and alignment such that each one of the images that are displayed in the two-dimensional plane shows a matching tissue region.

An image transformation command can be entered via a graphical user interface with respect to one of the displayed images, such as by performing a mouse click on the image, rotating a mouse wheel or performing a gesture that is entered via a touch-sensitive display screen. For example, the image transformation command is a command to zoom in or zoom out, to rotate or perform another image transformation such as by selecting a field of view.

In response to the entry of the image transformation command to transform the one of the displayed images the other images are simultaneously transformed in the same way. This is done using the geometrical transformations, such as the mappings, that have been generated by the image registration algorithm. As a consequence, the image transformation is executed in unison in response to the image transformation command in all of the images.

Embodiments of the present invention are particularly advantageous as a user, such as a pathologist, can readily view and manipulate images obtained from tissue slices of a tissue region in an intuitive way that facilitates the task of performing a diagnosis.

In accordance with embodiments of the invention at least one of the tissue slices is marked by multiple stains for the acquisition of a multi-channel image. The multi-channel image is unmixed to provide a set of unmixed images. The unmixed images do not need to be registered with respect to each other or with respect to the multi-channel image as they are all based on the identical dataset that is acquired by the optical sensor from one of the tissue slices. The multi-channel image is selected as a reference image for performing the image registration algorithm with respect to the multiple images, excluding the set of unmixed images. This provides a mapping of each one of the multiple images to the reference image, except for the unmixed images.

Using the multi-channel image as a reference image for the image registration is advantageous as it reduces the computational cost of performing the image registration and the alignment of the images as no image registration and alignment is required for the unmixed images In accordance with an embodiment of the invention the image transformation command is a zoom in or a zoom out command that is received via the graphical user interface using gesture recognition. For example, the user's gesture by which the zoom in or zoom out image transformation command is entered is a pinch gesture that is performed by placing two fingers onto one of the displayed images. The image transformation command is thus received with respect to the one of the displayed images on which the user places his or her fingers and is executed with respect to this image and also synchronously with respect to the other displayed images.

In accordance with a further embodiment of the invention the acquired multiple images are stored on a server computer. The images are transmitted from the server computer to a mobile battery-powered telecommunication device, such as a smartphone or mobile computer, via a telecommunication network for displaying the images on a display of the telecommunication device. This provides an utmost degree of flexibility as regards access and viewing of the images.

In accordance with an embodiment of the invention at least the execution of the image registration algorithm is performed by the server computer and the resultant geometrical transformation, such as the mappings, are transmitted together with the images from the server computer to the telecommunication device. This may be advantageous as the image registration algorithm may require substantial computational processing power. Executing the image registration algorithm as a preprocessing step by the server computer and not on the mobile battery-powered telecommunication device has the advantage of saving battery power and reducing the latency time experienced by the user.

In accordance with embodiments of the invention one or more fields of view are defined automatically in one or more of the images. A graphical symbol, such as a rectangular box, may be displayed in order to indicate the location of the field of view in one of the images. A user may enter an image transformation command with respect to a field of view by selecting the respective graphical symbol such as by touching the graphical symbol on a touch-sensitive display. In response to the selection of the graphical symbol a zoom in image transformation may be executed with respect to the field of view and synchronously with respect to aligned image portions in the other images.

The automatic definition of the fields of view may also be performed by the server computer in order to reduce the computational burden of the telecommunication device, thus increasing battery lifetime and decreasing latency times. In this instance meta data that is descriptive of the defined fields of view is generated by the server computer and transmitted together with the images via the network in order to enable the telecommunication device to display the graphical symbol indicating the location of a field of view defined by the server computer.

In accordance with a further aspect of the invention an image processing system is provided that is configured to execute a method of the invention.

The present invention is surprisingly effective to allow a coordinated review of a multiplicity of diagnostic images of the same tissue region that are shown adjacent to one another on a single viewing screen. All images are aligned and scaled to a common reference frame, and they can all be translated and zoomed together, each showing an important aspect of histology. This enables a more directed and determined diagnosis of important conditions, where any single image might only support a more tentative conclusion from an expert reader.

The present invention has at least the following advantageous features and robustness:

1. A common display reference frame is chosen and used for image visualization.

2. The preprocessed images of the biological tissue sample are converted to the common display reference frame by constructing a destination view for each preprocessed image in order to produce displayable images.

3. User gestures are accepted to dynamically alter the common display reference frame. For example, the images can be simultaneously translated, rotated, or zoomed in magnification.

4. When each image shows a different staining to highlight important aspects of the biological tissue sample, the simultaneous views offer a more certain diagnosis of tissue conditions than could be had by relying on the memory of the expert reader conducting a serial inspection of these same images.

The present invention further accommodates images that are derived from consecutive microtome slices, where they may require rotation in addition to translation to align common features of interest. Also, the present invention may involve tagging images with metadata to describe their location in a tissue section, and this this information is used for construction of affine transforms to adjust the images to a common reference frame for display. Additionally, the present invention allows for simultaneous zooming in magnification of all images at the same scale.

In one embodiment, the subject disclosure features a system of simultaneously displaying multiple views of a same region of a biological tissue sample. The system may comprise a processor and a memory coupled to the processor. The memory can store computer-readable instructions that, when executed by the processor, cause the processor to perform operations.

In another embodiment, the subject disclosure features a method of simultaneously displaying multiple views of a same region of a biological tissue sample. The method may be implemented by an imaging analysis system and may be stored on a computer-readable medium. The method may comprise logical instructions that are executed by a processor to perform operations.

In some embodiments, the operations may include receiving a plurality of preprocessed images of the biological tissue sample, choosing a common display reference frame that is used for image visualization, converting the plurality of preprocessed images to the common display reference frame by constructing a destination view for each preprocessed image of the plurality of preprocessed images to produce a plurality of displayable images, arranging the plurality of displayable images into a display pattern for viewing on the display screen, displaying the plurality of displayable images on a display screen, and accepting user gestures to dynamically alter the common display reference frame.

In yet other embodiments, the operations may further include translating, rotating, and zooming in and out of the plurality of images in unison on the display screen in response to an input gesture from an interface device to provide a desired perspective of the imaged biological tissue sample, removing one or more images from the plurality of images on the display screen to declutter the display screen, adding new mode images onto the display screen, rearranging the display pattern to form an alternative display pattern, stacking two or more image modes to reinforce image features, and saving the display pattern of a current examination as a saved template for future examinations.

In one enablement of this patent, collections of pre-registered images might be provided by the FOV analysis. Examples of FOV analysis are described herein. The images are tagged with metadata describing their individual placement, rotation, and magnification, with respect to a common frame of reference. Together with any new reference frame, the metadata may define an affine mapping between original reference frame of the image and the new frame.

Reimaging to the new frame may be accomplished by mapping a destination pixel in the new frame back to its corresponding location in the source frame of an image, and choosing that pixel value, or a an interpolation of surrounding source pixel values, as the destination pixel value. In this way, any image can be translated, rotated, stretched, or shrunk to the new reference frame shared by all other images in preparation for simultaneous display.

Deciding which arrangements are important for a diagnostician may be based entirely on the best judgement of the expert reader. Some views may be deemed unimportant for the case at hand, while still others might be added to the collection as being more important for diagnosis.

Embodiments of the present invention are particularly advantageous as an automatic and reliable technique is provided to identify fields of view in a multi-channel image while avoiding the tedious effort of manually marking fields of view in a multi-channel image by a pathologist or biologist and thereby also eliminating subjective judgment and human error. As the spatial low pass filtering, the local maximum filtering and thresholding operations can be executed at high processing speeds, the computational expense and the latency time experienced by the user can be minimized. This is due to the fact that the definition of the fields of view is not performed directly on the multi-channel image but on the basis of the filtered and thresholded image which enables the high processing speed.

It is to be noted that the analysis in step f is executed on the full resolution multi-channel image and not on the spatial low pass filtered unmixed image. This assures that the full amount of the available pictorial information can be used for performing the analysis while the filtering operation, namely steps b, c and d, merely serve for identification of the relevant fields of view where a full analysis is to be performed.

In accordance with a further embodiment of the invention one of the unmixed images is processed for defining the field of view as described above while another one of the unmixed images is segmented for identification of tissue regions. The unmixed image can be generated from a single stain image (2-channel, e.g. embodiment of FIG. 2 with a stain and a counter-stain) or from a multiplex image (more than 2 channels).

Suitable segmentation techniques are as such known from the prior art, (cf. Digital Image Processing, Third Edition, Rafael C. Gonzalez, Richard E. Woods, chapter 10, page 689 and Handbook of Medical Imaging, Processing and Analysis, Isaac N. Bankman, Academic Press, 2000, chapter 2). By means of the segmentation non-tissue regions are removed as the non-tissue regions are not of interest for the analysis.

The segmentation provides a mask by which those non-tissue regions are removed. The resultant tissue mask can be applied onto the unmixed image prior or after the spatial low pass or local maximum filtering or thresholding operations and before or after the fields of view are defined. It may be advantageous to apply the tissue mask at an early stage in order to further reduce the processing load, such as before the execution of the spatial low pass filtering.

In accordance with an embodiment of the invention the other one of the unmixed images that is segmented for providing the tissue mask is obtained from the channel that is representative of one stain that is a counter-stain to the stain represented by the unmixed image that is processed in accordance with steps b-e of claim 1.

In accordance with an embodiment of the invention fields of view are defined for at least two of the unmixed images. Fields of view that are defined in two different unmixed images can be merged if they are located at the same or almost identical image location. This is particularly advantageous for stains that can be co-located such that a single field of view results for the co-located stains that identify a common biological structure. By merging such fields of view the processing load is further reduced and the analysis in step f needs only to be performed once for the merged field of view. Moreover, the cognitive burden for the pathologist or biologist is also reduced as only one analysis result is presented rather than two related results. Depending on the implementation, the two fields of view may be merged if a degree of spatial overlap of the fields of view is above an overlap threshold.

In accordance with embodiments of the invention the analysis of the field of view is performed by cell counting of the biological cells shown in the multi-channel image within the considered field of view. The cell counting can be performed by using a suitable image analysis technique which is applied on the field of view. In particular, the cell counting can be executed by means of an image classification technique.

In accordance with further embodiments of the invention the analysis of the field of view is performed by means of a trained convolutional neural network such as by entering the field of view or an image patch taken from the field of view into the convolutional neural network for determining a probability for the presence of a biological feature within the field of view or the image patch, respectively. An image patch may be extracted from the field of view for entry into the convolutional neural network by first identifying an object of interest within the field of view and then extracting the image patch that contains this object of interest.

In accordance with a further embodiment of the invention the analysis is performed on the field of view in step f as a data analysis, such as a cluster analysis or statistical analysis.

In accordance with another aspect of the invention an image processing system for analyzing a multi-channel image obtained from a biological tissue sample being stained by multiple stains is provided that is configured to execute a method of the invention.

The subject disclosure features preprocessing systems and methods for automatic field of view (FOV) selection based on a density of each cell marker in a whole slide image. Operations described herein include reading images for individual markers from an unmixed multiplex slide or from singularly stained slides, and computing the tissue region mask from the individual marker image.

A heat map of each marker may be determined by applying a low pass filter on an individual marker image channel, and selecting the top K highest intensity regions from the heat map as the candidate FOVs for each marker. The candidate FOVs from the individual marker images are merged together. The merging may comprise one or both of adding all of the FOVs together in the same coordinate system, or only adding the FOVs from the selected marker images, based on an input preference or choice, by first registering all the individual marker images to a common coordinate system and merging through morphologic operations. After that, all of the identified FOVs are transferred back to the original images using inverse registration to obtain the corresponding FOV image at high resolution.

In some embodiments, lower-resolution images are used to speed computation of the FOVs. Because the images are lower resolution, it is computationally much faster to compute the heat map and tissue region mask. This allows the selection of the FOVs to be made automatic and rapid, which allows for faster analysis of the tissue sample.

Tissue slide images contain many features, only some of which are of interest for any particular study. Those interesting regions may have a specific color brought about by selective stain uptake. They may also have broad spatial extent. Importantly, the uninteresting regions may have some specific spatial frequencies that enable their removal from an image by way of spatial frequency filtering. Such filters include, but are not limited to, low pass, high pass, and band pass, filters. More carefully tuned spatial frequency filters may be those known as matched filters. Non-limiting examples of spatial frequency filters include, but are not limited to, low pass filters, high-pass filters, band-pass filters, multiple-passband filters, and matched filters. Such filters may be statically defined, or adaptively generated.

In the process of locating regions of interest, it is therefore helpful to first select the proper color by an unmixing process, which can be viewed as a linear operator applied to the primary color channels, R, G, and B, of the image. Spatial frequency filtering is also applied to give preference to features of interest in the image. These operations may be applied in either order since they are both linear operators.

In parallel with this region selection, there may be a broader segmentation mask formed by using entirely differently tuned spatial frequency filters, to select, for example, only the gross region of the slide image where tissue resides, and rejecting empty regions. Therefore, multiple different spatial frequency filters may be applied to the same tissue slide image.

Once filtered, a region of interest may be located by applying a local max filter, a kind of morphological nonlinear filter, which produces an image by making each pixel of the result hold the value of the maximum pixel value from the source image that lies beneath the kernel of the max filter. The kernel is a geometric mask of arbitrary shape and size, but would be constructed for this purpose to have dimensions on the order of the interesting features. The output image from a local max filter will tend to have islands shaped like the kernel and with constant values equal to the maximum pixel value in that region.

In some embodiments, with the present construction of a local max filter image, a threshold may be applied to convert the filter image to a binary mask, by assigning binary mask values of 1 to corresponding filter image pixels above the threshold, and values of 0 to corresponding filter image pixels below the threshold. The result will be blobs of 1's that can be labeled as regions, and with measurable spatial extents. Together, these region labels, locations, and spatial extents provide a record of regions of interest (ROIs), or fields of view (FOVs).

BRIEF DESCRIPTION OF THE DRAWINGS

FIGS. 5A-5B depict merging of FOVs from all markers and from selected markers, respectively, according to an exemplary embodiment of the subject disclosure.

DETAILED DESCRIPTION OF THE SUBJECT DISCLOSURE

The present invention features a system and method of simultaneously displaying multiple views of a same region of a biological specimen, for example, a tissue sample. In some embodiments, the system may comprise a processor and a memory coupled to the processor. The memory can store computer-readable instructions that, when executed by the processor, cause the processor to perform operations.

In other embodiments, the method may be implemented by an imaging analysis system and may be stored on a computer-readable medium. The method may comprise logical instructions that are executed by a processor to perform operations.

Figure 14:
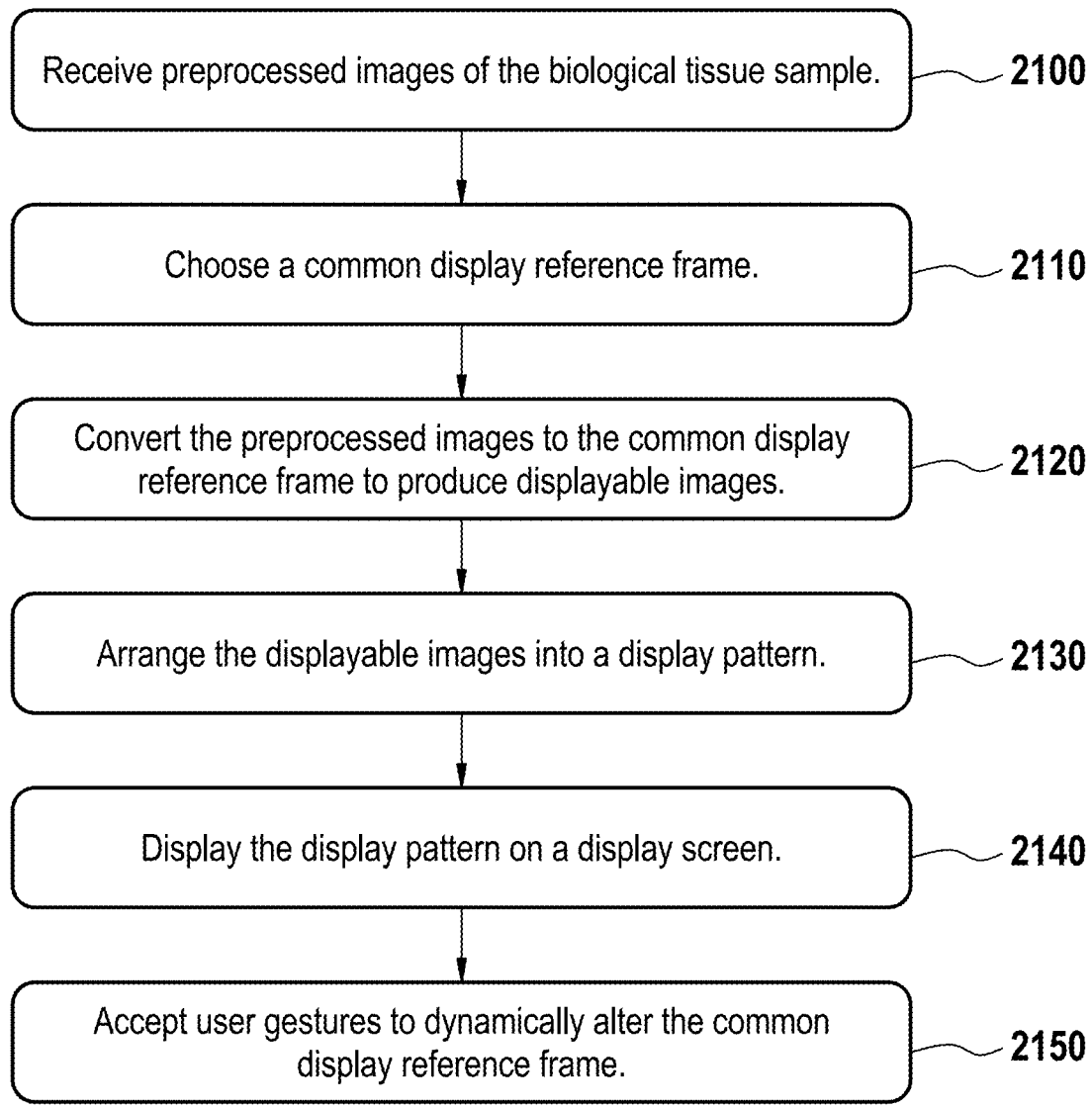
FIG. 14 depicts an exemplary process flow chart for simultaneously displaying multiple views according to an embodiment of the present invention.

As shown in FIG. 14, operations for the system and method described herein can include, but are not limited to, receiving a plurality of preprocessed images of the biological tissue sample (2100), choosing a common display reference frame that is used for image visualization (2110), converting the plurality of preprocessed images to the common display reference frame by constructing a destination view for each preprocessed image of the plurality of preprocessed images to produce a plurality of displayable images (2120), arranging the plurality of displayable images into a display pattern for viewing on the display screen (2130), displaying the plurality of displayable images on a display screen (2140), and accepting user gestures to dynamically alter the common display reference frame (2150). Without wishing to limit the present invention to a particular theory or mechanism, the present invention allows for a coordinated review of the plurality of images that are shown adjacent to one another on a single viewing screen.

In some embodiments, displaying of the plurality of displayable images (2140) may allow for simultaneous dynamic viewing of different aspects of the imaged biological tissue sample. Repeating the conversion process (2120) may cause all displayable images to simultaneously perform apparent coordinated translation, rotation, or magnification changes.

In some embodiments, each preprocessed image may show a view mode of a same region of the biological tissue sample, and each preprocessed image may have metadata that describe an image reference frame with respect to a global standard reference frame. The metadata of each preprocessed image may describe a preprocessed image local reference frame (PI-LRF) with respect to a global standard reference frame (GSRF). For example, the metadata may describe the spatial location, orientation, and magnification of the preprocessed image with respect to the global standard reference frame. As another example, the metadata describes translation, rotation, and magnification of each image with respect to a standard reference frame. By knowing the common display reference frame, an affine transformation is created to associate source image pixels to displayed pixels for an image mode view. As used herein, an affine transformation or, alternatively, an affine mapping, can be defined as a linear transform, expressible as a matrix operator against augmented position vectors, which can express arbitrary translations, rotations, and magnifications, of those vectors. Affine transformations are known to one of ordinary skill in the art.

In some embodiments, the preprocessed image local reference frame (PI-LRF) is a two-dimensional reference frame used to describe a location of a pixel in the preprocessed image.

In other embodiments, the global standard reference frame is an agreed-upon, fixed two-dimensional reference frame used to describe a space of pixel locations and which allows an understanding of spatial relationships between different images by defining affine mappings between each image local reference frame (I-LRF) and the global standard reference frame. In some embodiments, the metadata of each preprocessed image describe the spatial location, orientation, and magnification of the preprocessed image with respect to the GSRF. For example, the metadata can define a first affine mapping between the image reference frame and the global standard reference frame.

Figure 15:
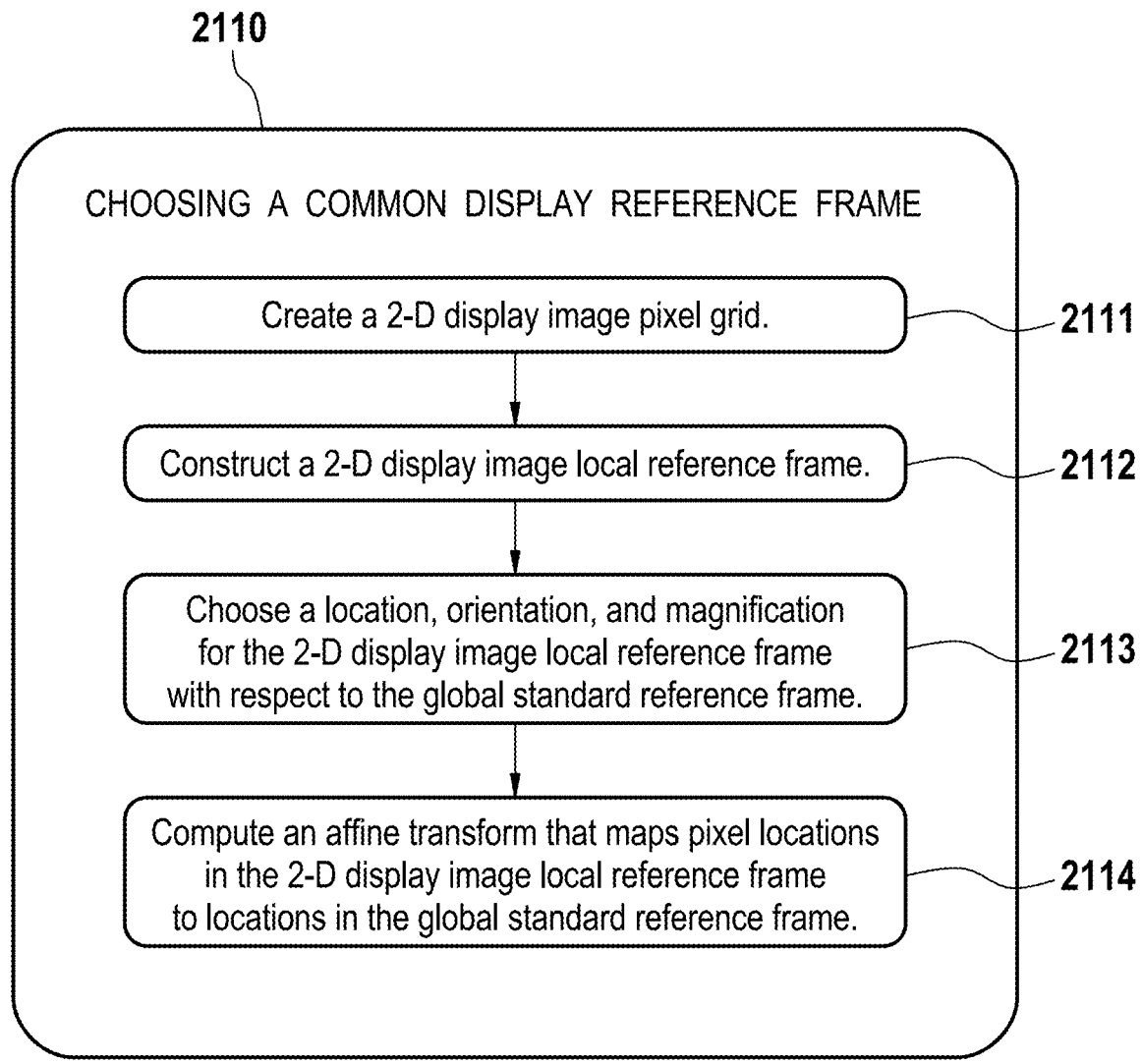
FIG. 15 depicts an exemplary process flow chart for choosing a common display reference frame according to an embodiment of the present invention

In some embodiments, as shown in FIG. 15, the operation of choosing a common display reference frame (2110) may further comprise creating a two-dimensional display image pixel grid (2111), constructing a two-dimensional display image local reference frame (DI-LRF) used to describe pixel locations in the display image pixel grid (2112), choosing a location, orientation, and magnification for the DI-LRF with respect to the GSRF (2113), and computing an affine transform that maps pixel locations in the DI-LRF to locations in the GSRF (2114). The grid intersections can denote pixel locations. This construction can serves as a display image template and may provide an affine partial mapping for production of display images.

Figure 16:
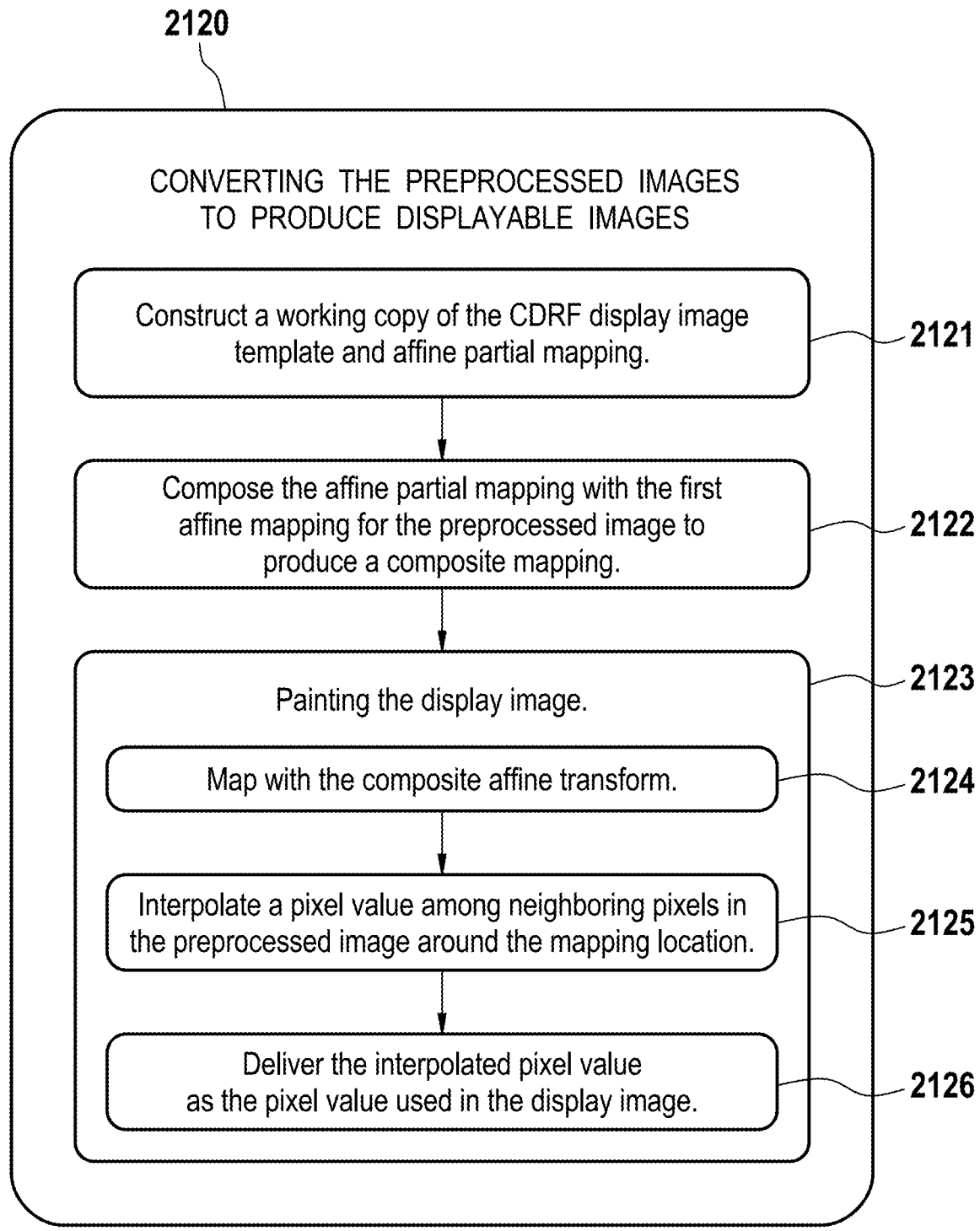
FIG. 16 depicts an exemplary process flow chart for converting preprocessed images to produce displayable images according to an embodiment of the present invention.

In some embodiments, as shown in FIG. 16, the operation of converting the plurality of preprocessed images to the common display reference frame (2120) may further comprise constructing a working copy of the CDRF display image template and affine partial mapping (2121), composing the affine partial mapping with the first affine mapping for the preprocessed image to produce a composite mapping that transforms pixel locations in the DI-LRF of the display image to a location in the PI-LRF of the preprocessed image (2122), and painting the display image by performing operations for each display image pixel (2123). In some embodiments, the working copy of the display image template comprises memory cells to hold pixel values for a display image.

Operations for painting the display image may include, but are not limited to, mapping with the composite affine transform from a DI-LRF location of the display image pixel to a location in the PI-LRF of the preprocessed image (2124), interpolating a pixel value among neighboring pixels in the preprocessed image around that mapped location (2125), and delivering the interpolated pixel value as the pixel value used in the display image at the display image pixel (2126). By performing these operations for each display image pixel, each preprocessed image may be transformed to the display image for representation on the display screen.

In some embodiments, interpolation among neighboring pixels (2125) may be performed by simply choosing the nearest pixel for its value, or by using bilinear interpolation among the four nearest neighboring pixels. In other embodiments, when magnification is changed between source and target images, more elaborate methods, such as spatial low-pass filtering, may be required to avoid sample aliasing or imaging artifacts, since this is equivalent to sample rate conversion.

In other embodiments, the operation of converting the plurality of preprocessed images (2120) may perform nonlinear corrections on the plurality of preprocessed images to remove optical distortions. Exemplary nonlinear corrections may include removal of pincushion or barrel distortion, defocus, coma, or astigmatism.

In some embodiments, any of the two-dimensional reference frames as mentioned herein, such as the two-dimensional local reference frames (PI-LRFs and the DI-LRF) and the agreed-upon fixed two-dimensional reference frame (GSRF), can be orthogonal Cartesian reference frames. In other embodiments, any of the two-dimensional reference frames as mentioned herein can be non-orthogonal and/or non-Cartesian reference frames.

In some embodiments, the plurality of images is produced by preprocessing images of the biological tissue sample. Preprocessing of the images may utilize methods such as the FOV methods as described herein. However, it is understood that other suitable methods may be used to preprocess the images.

In some embodiments, the display pattern may be in the form of rows and columns. This display pattern may feature an "m" number of rows and an "n" number of columns, where "m" and "n" can be any natural number. For example, the display pattern may have 2 rows and 3 columns. In other embodiments, the display pattern may be a ring or a square. In still other embodiments, the display pattern may be a pyramid.

Figure 17:
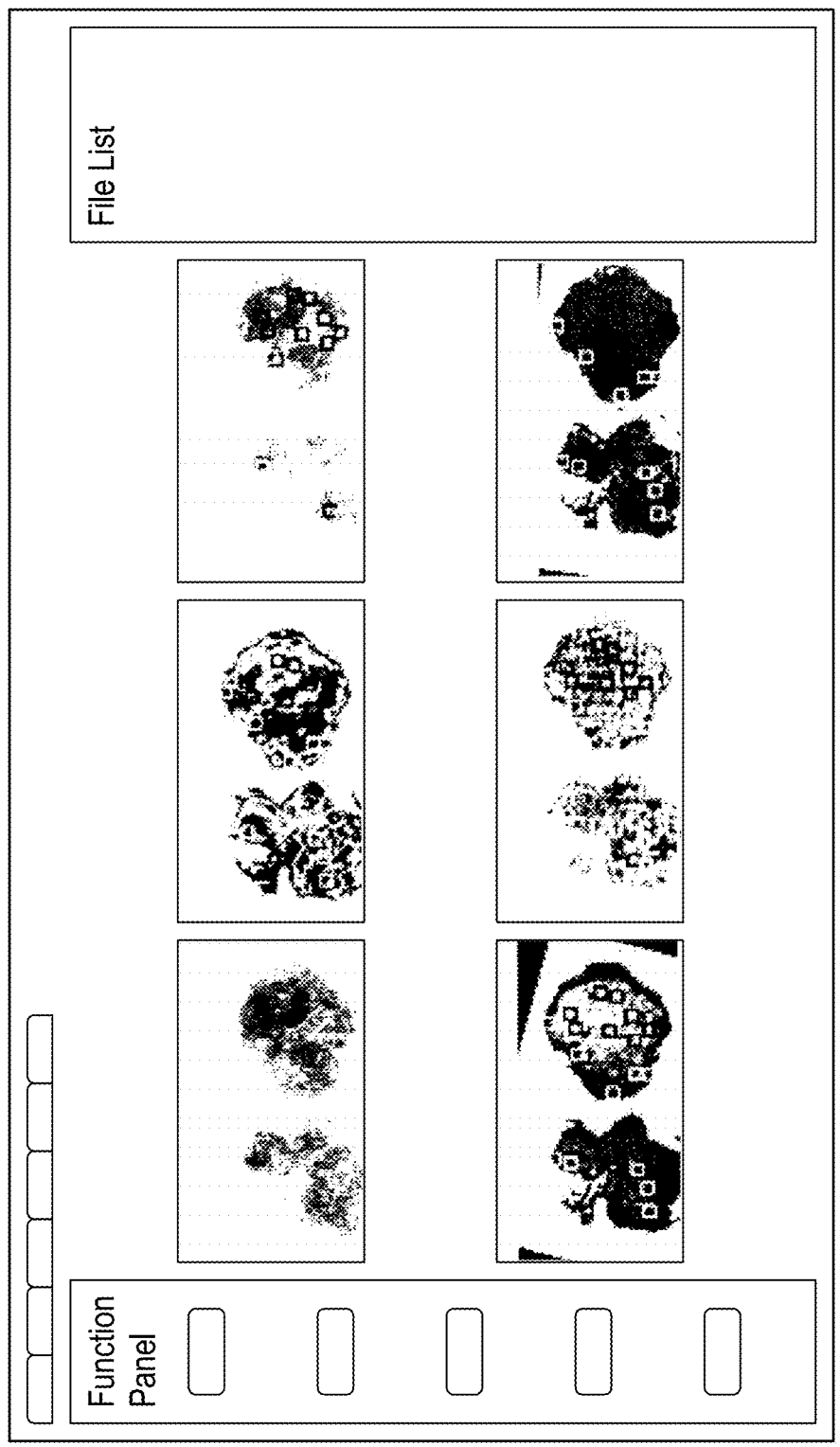
FIG. 17 depicts a translated view of images on a user interface according to an exemplary embodiment of the subject disclosure.
Figure 18:
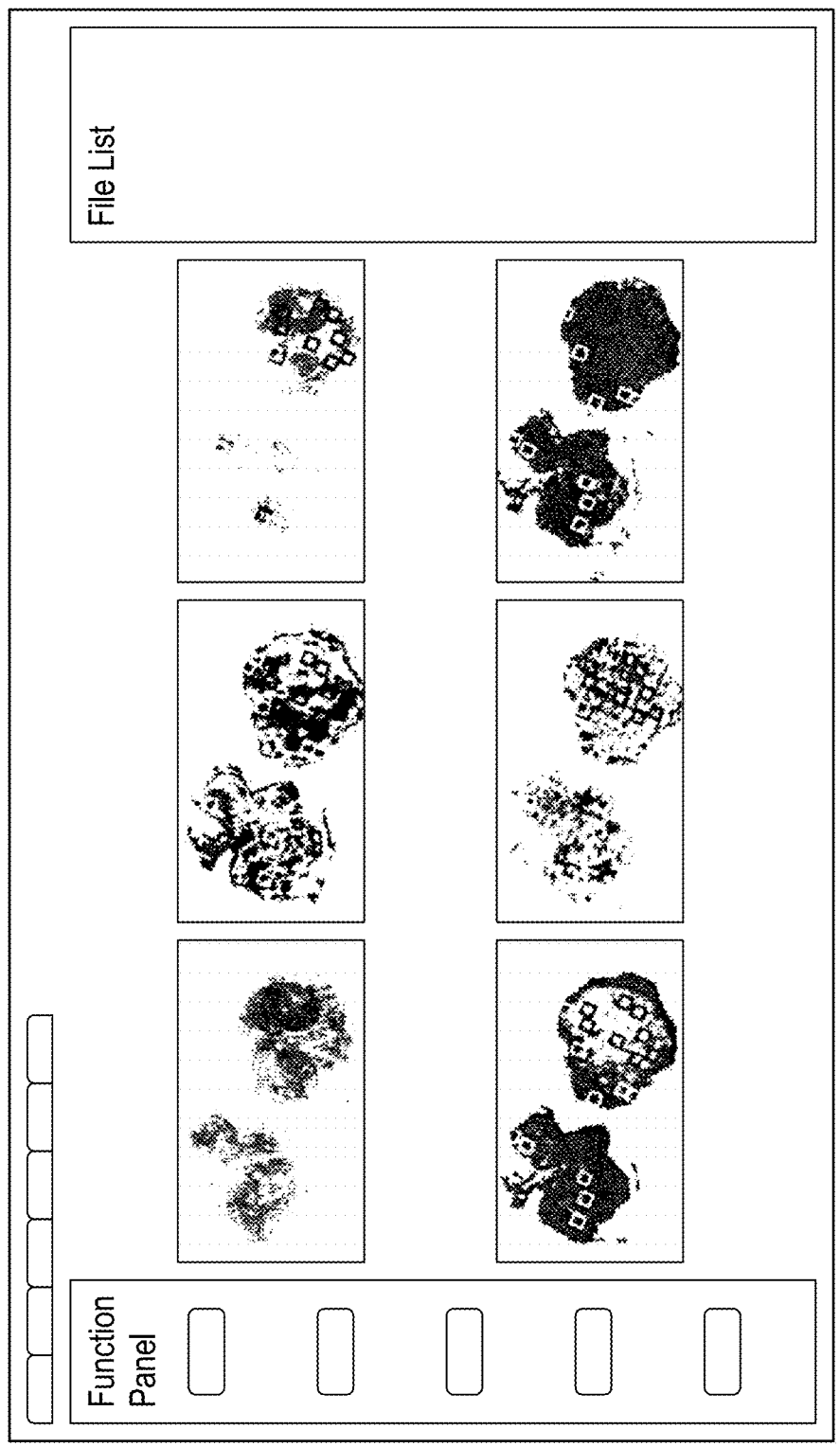
FIG. 18 depicts a rotated view of images on a user interface according to an exemplary embodiment of the subject disclosure.
Figure 19:
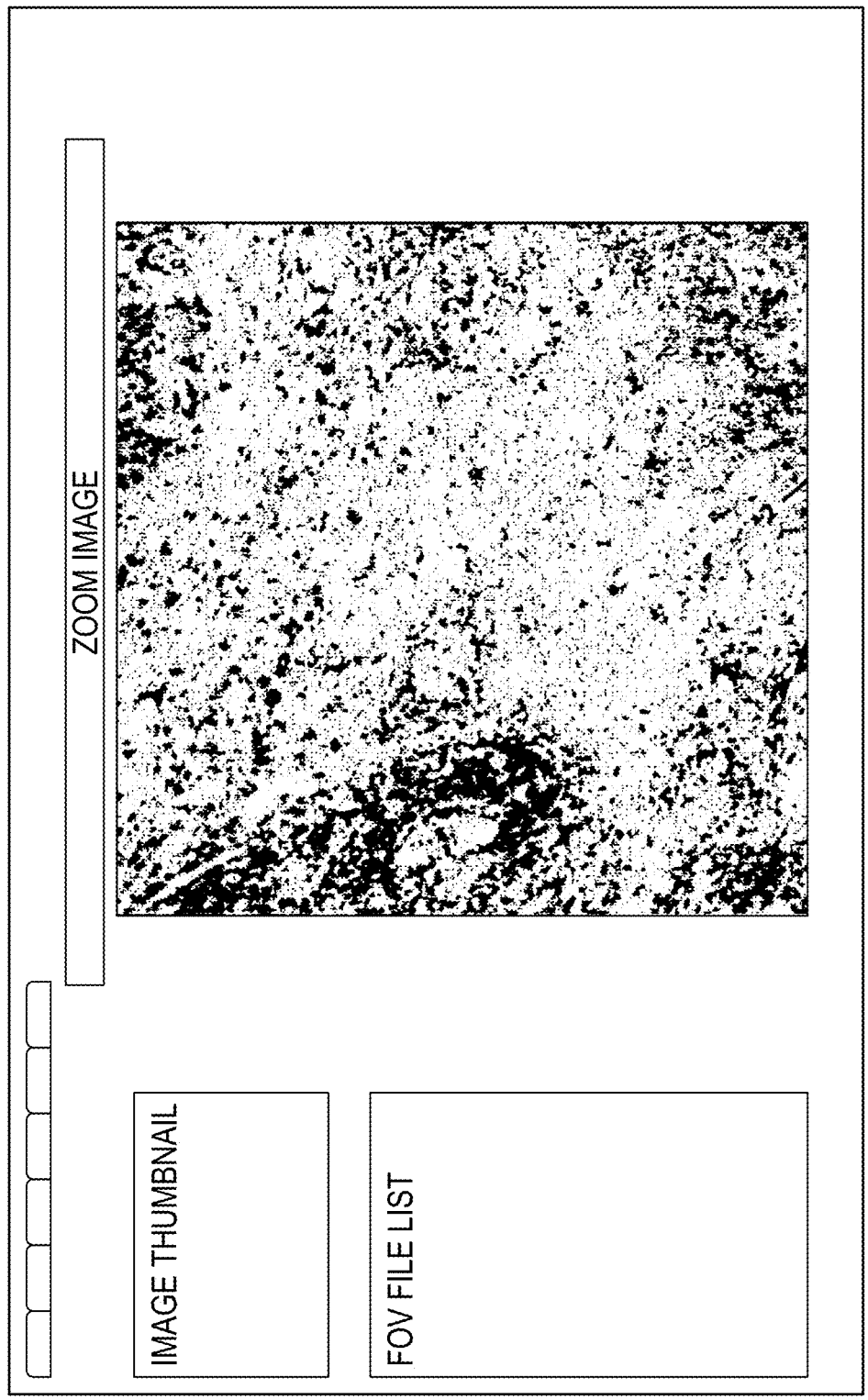
FIG. 19 depicts two images deleted from a user interface according to an exemplary embodiment of the subject disclosure.

In other embodiment, the operations may further comprise translating the plurality of images in unison on the display screen in response to an input gesture from an interface device, rotating the plurality of images in unison on the display screen in response to an input gesture from an interface device, and zooming in and out of the plurality of images in unison on the display screen in response to an input gesture from an interface device. As shown in FIGS. 17-19, the operations of translating, rotating, and zooming of the plurality of images may provide a desired perspective of the imaged biological tissue sample. For example, translating of the plurality of images may involve sliding the images in a linear direction. Rotation of the plurality of images may be performed in a clockwise or counterclockwise direction. Zooming in on the plurality of images may provide for a closer view of a region of the biological tissue sample. Zooming out of the plurality of images may provide for a distant view of the biological tissue sample.

Figure 20:
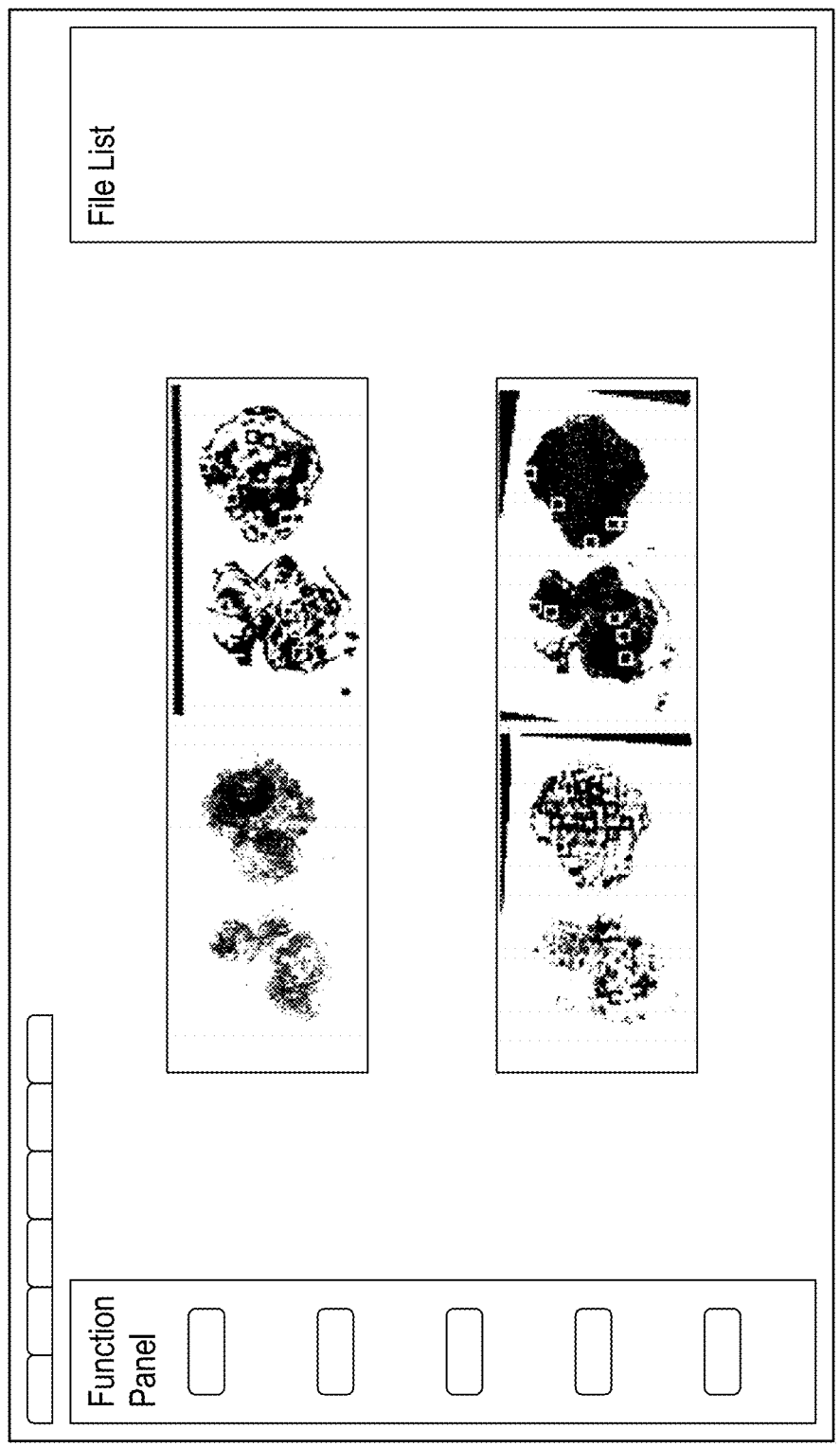
FIG. 20 depicts a rearranged display pattern of images on a user interface according to an exemplary embodiment of the subject disclosure.

In some embodiments, as shown in FIG. 20 the operations may further comprise removing one or more images from the plurality of images on the display screen to declutter the display screen. For example, if an image shows an undesirable or irrelevant view of the biological tissue sample, the image may be removed. In other embodiments, the operations may further comprise adding new mode images onto the display screen. The new mode images may be viewed in tandem with other image modes.

Non-limiting examples of modes in which images may be viewed can include a variety of color channels, image filter states, or edge detection states. Generally, there may be useful alterations of an original image that highlight certain characteristics, which could offer simultaneous views containing important features of diagnostic interest to the expert reader.

Figure 21:
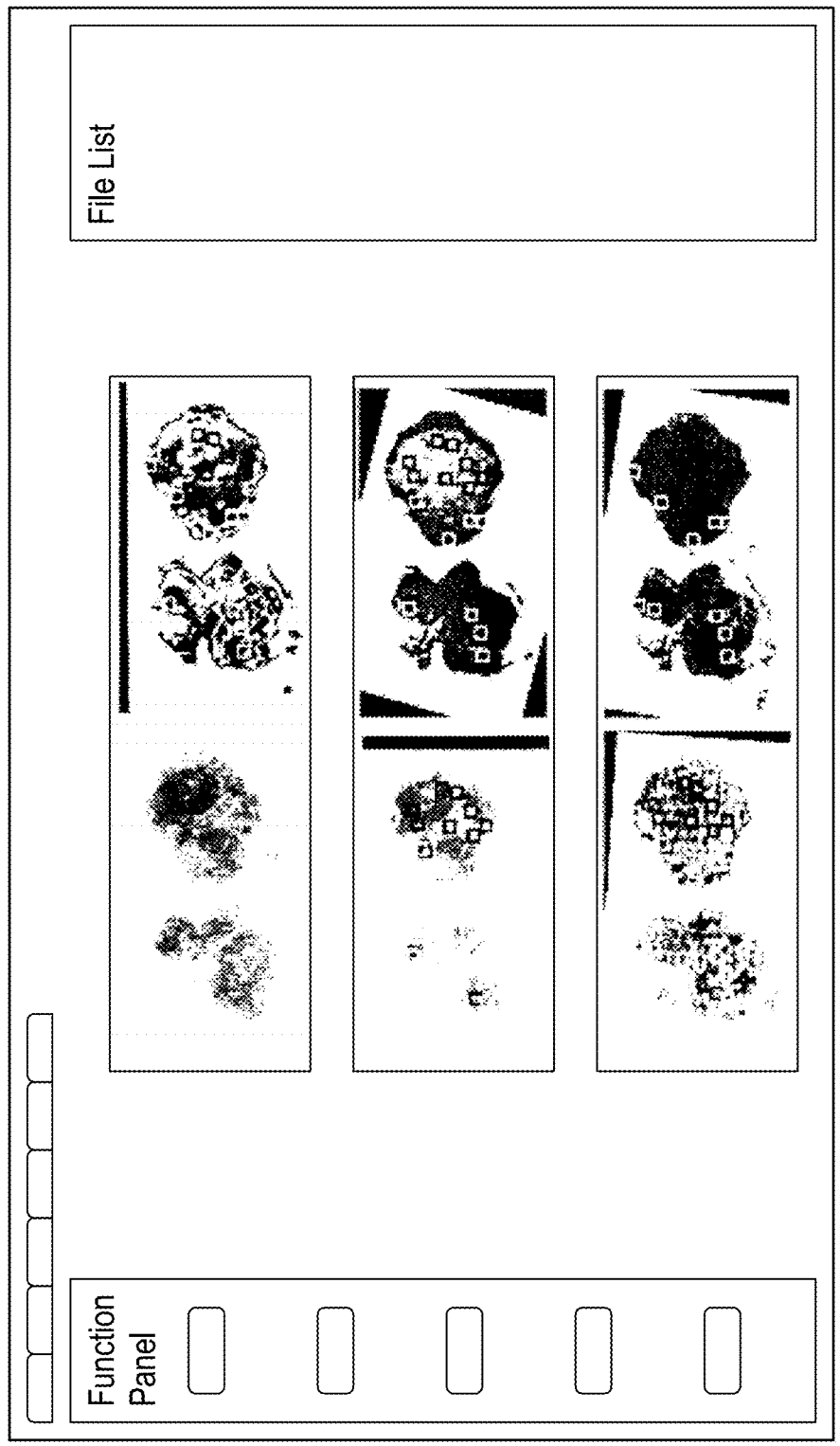
FIG. 21 depicts a zoomed in view of an image on a user interface according to an exemplary embodiment of the subject disclosure.
Figure 22:
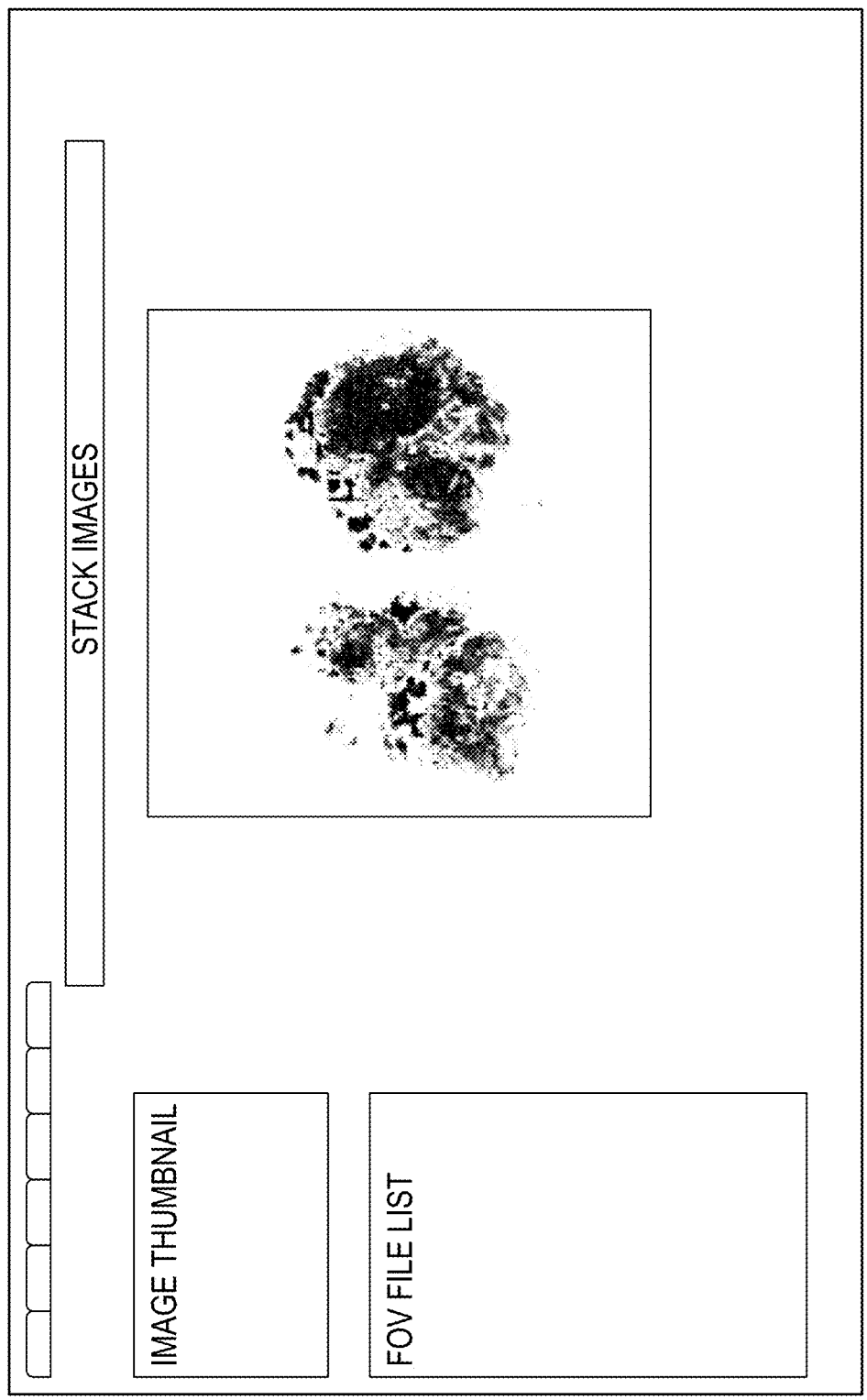
FIG. 22 depicts a stacked view of two images on a user interface according to an exemplary embodiment of the subject disclosure.

In some embodiments, as shown in FIG. 21, the operations may further comprise rearranging the display pattern to form an alternative display pattern. The alternative display pattern may bring together image modes for closer inspection. In other embodiments, as shown in FIG. 22, the operations may further comprise stacking two or more image modes to reinforce image features. Stacking of the two or more image modes can be in response to an input gesture from an interface device. In some embodiments, the two or more image modes may be translucent.

In other embodiments, the operations may further comprise saving the display pattern of a current examination as a saved template to facilitate displaying of another plurality of images in future examinations.

In one embodiment of this invention, the expert reader can affect all images simultaneously by invoking actions on only one of the images such that all images respond in tandem. Non-limiting exemplary input gestures and interface devices may include, but are not limited to, a mouse, a haptic sensor, eye sensors, and electronic cameras. For example, an expert reader might use a mouse click to activate one of the images, and then rotate the mouse wheel to affect zoom magnification of the images. Mouse click and drag within an activated image might drag all images in the same direction. As another example, a haptic sensor might be used to perform selected image changes. The haptic sensor may offer rotation, translation, zooming, stacking, etc, which may be more elaborate than a simple computer mouse.

Eye sensors can detect eye gestures of the expert reader, such as changing the center of sight attention, blinking, etc. Electronic cameras can witness special gestures of an operator, such as hand motion, that indicate image translation, rotation, magnification, display rearrangement, image stacking, and control of translucence during stacking, etc. In other embodiments, any sufficient and valid manner of interacting with a device, such as a computer, may be used, with a preference for the simplest and most direct interaction to achieve the expert reader's aims.

In alternative embodiments, the method of simultaneously displaying multiple views of a same region may be used in examination of multispectral Earth surface imagery for remote sensing applications, or for battlefield management.

A non-limiting example of implementing the method of simultaneously displaying multiple views of a same region of a biological tissue sample on a display screen may feature:
1. Loading data for the biological tissue sample.
2. Selecting a file from a file list.
3. Displaying six images from the selected file in a display pattern of 3 columns by 2 rows.
4. Selecting important markers.
5. Displaying a heat map for a marker of the image sample.
6. Switching between an original view, a heat map view, or an individual marker view.
7. Displaying hot spots of the image sample.
8. Aligning to a same coordinate system.
9. Rotating, translating, or zooming in and out of the images.
10. Merging the FOVs.
11. Assigning a label to a region of the imaged sample.
12. Renaming an image.
13. Adding or deleting images.
14. Saving the file.

Preprocessing of Images

In some embodiments, the present invention may utilize systems and methods for preprocessing of biological slide images. It is understood that any suitable system or method may be used to preprocess the images. In one embodiment, a non-limiting example of a preprocessing system or method may feature an automatic field of view (FOV) selection based on a density of each cell marker in a whole slide image. Operations described herein include, but are not limited to, reading images for individual markers from an unmixed multiplex slide or from singularly stained slides, and computing the tissue region mask from the individual marker image. A heat map of each marker may be determined by applying a low pass filter on an individual marker image channel, and selecting the top K highest intensity regions from the heat map as the candidate FOVs for each marker. The candidate FOVs from the individual marker images may then be merged together. The merging may comprise one or both of adding all of the FOVs together in the same coordinate system, or only adding the FOVs from the selected marker images, based on an input preference or choice, by first registering all the individual marker images to a common coordinate system and merging through morphologic operations. Subsequently, all of the identified FOVs are transferred back to the original images using inverse registration to obtain the corresponding FOV image at high resolution. Without wishing to limit the present invention to any theory or mechanism, the systems and methods of the present invention may offer advantages such as being reproducible, unbiased to human readers, and more efficient.

In some embodiments, the system for quality control of automated whole-slide analysis comprises an image acquisition system (102), a processor (105); and a memory coupled to the processor (110). The memory is configured to store computer-readable instructions that, when executed by the processor, cause the processor to perform operations one or more of the following operations (but not limited to the following operations) comprising: reading a high resolution input image (231) from the image acquisition system (102), computing a low resolution version of the high resolution input image, reading a plurality of low resolution image marker images from the image acquisition system (102), wherein each image marker image is of a single color channel (232) of the low resolution input image, computing a tissue region mask (233) corresponding to the low resolution input image, computing a low pass filtered image (234) of each image marker image (114), generating a masked filtered for each image marker image (113), where the masked filtered image is the tissue region mask multiplied by the low pass filtered image, identifying a plurality of candidate fields of view (FOVs) within each masked filtered image (116), merging a subset of a plurality of candidate FOVs for each image marker image (117), into a plurality of merged FOVs, and depicting the merged portion of the plurality of candidate fields of view on the input image.

In some embodiments, a heat map may be computed for the masked filtered image. In some embodiments, the heat map comprises applying colors to the masked filtered image, wherein low intensity regions are assigned to blue colors and higher intensity regions are assigned to yellow orange and red colors. Any other appropriate colors or combinations of colors may be used to assign low and high intensity regions.

In some embodiments, the generation of the tissue region mask comprises one or more of the following operations (but not limited to the following operations): computing the luminance (337) of the low resolution input image (336), producing a luminance image (338), applying a standard deviation filter to the luminance image (339), producing a filtered luminance image (340), and applying a threshold to filtered luminance image (341), such that pixels with a luminance above a given threshold are set to one, and pixels below the threshold are set to zero, producing the tissue region mask (342).

In some embodiments, the tissue region mask is computed directly from the high resolution input image. In this case, the tissue region mask may be converted to a lower resolution image before application to the filtered image market images.

In some embodiments, the image marker images are obtained by unmixing (111) a multiplex slide, where the unmixing module uses a reference color matrix (112) to determine what colors correspond to the individual color channels. In other embodiments, the image marker images are obtained from single stain slides.

In some embodiments, the image registration process comprises selecting one image marker image to serve as a reference image, and computing a transformation of each image marker to the coordinate frame of the reference image. The methods for computing a transformation of each image to a reference image are well known to those skilled in the art. In other embodiments, if the images are obtained by unmixing a multiplex reference slide, no registration is needed since all the unmixed images are already in the same coordinate system.

The subject disclosure provides systems and methods for automatic field of view (FOV) selection. In some embodiments, the FOV selection is based on a density of each cell marker in a whole slide image. Operations described herein include reading images for individual markers from an unmixed multiplex slide or from singularly stained slides, and computing the tissue region mask from the individual marker image. A masked filtered image of each marker may be determined by applying a low pass filter on an individual marker image channel, and applying the tissue region mask. The top K highest intensity regions from the masked filtered image are selected as the candidate FOVs for each marker. The candidate FOVs from the individual marker images are merged together. The merging may comprise one or both of adding all of the FOVs together in the same coordinate system, or only adding the FOVs from the selected marker images, based on an input preference or choice, by first registering all the individual marker images to a common coordinate system and merging through morphologic operations. After that, all of the identified FOVs are transferred back to the original images using inverse registration to obtain the corresponding FOV image at high resolution. Without wishing to limit the present invention to any theory or mechanism, the systems and methods of the present invention may offer advantages such as being reproducible, unbiased to human readers, and more efficient. As a result, a digital pathology workflow for automatic FOV selection, in accordance with the subject disclosure, includes a computer-based FOV selection algorithm that automatically provides the candidate FOVs that may be further analyzed by a pathologist or other evaluator.

The operations described herein have been described, for exemplary purposes, in connection with the identification of immune cells, and for use in immunoscore computations. However, the systems and methods may be applicable to any type of image of a cell or biological specimen, and are applicable to determinations of type, density and location for any type of cell or group of cells. As used herein, the terms "biological specimen" and "biological tissue sample" may be used interchangeably. Moreover, besides cancerous tissue and immune markers, the subject disclosure is applicable to any biological specimen or tumor of any disease or non-disease state, and images of biological specimens that have been subjected to any type of staining, such as images of biological specimens that have been stained with fluorescent and non-fluorescent stains. Also, one of ordinary skill in the art would recognize that the order of the steps may vary from what is described herein.

Figure 1A:
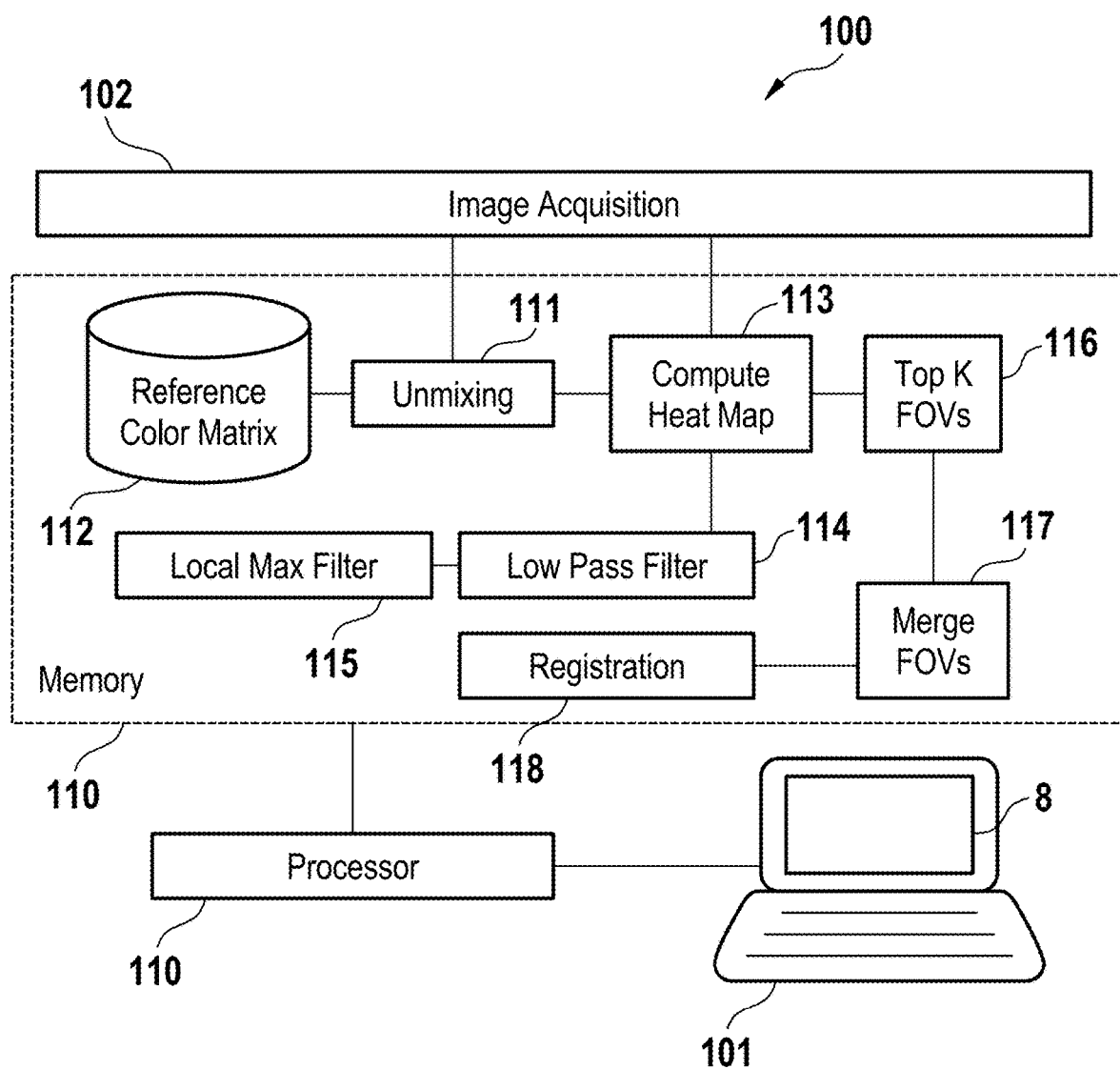
FIGS. 1A-1B respectively depict a system and a workflow for automatic FOV selection, according to an exemplary embodiment of the present subject disclosure.
Figure 1B:
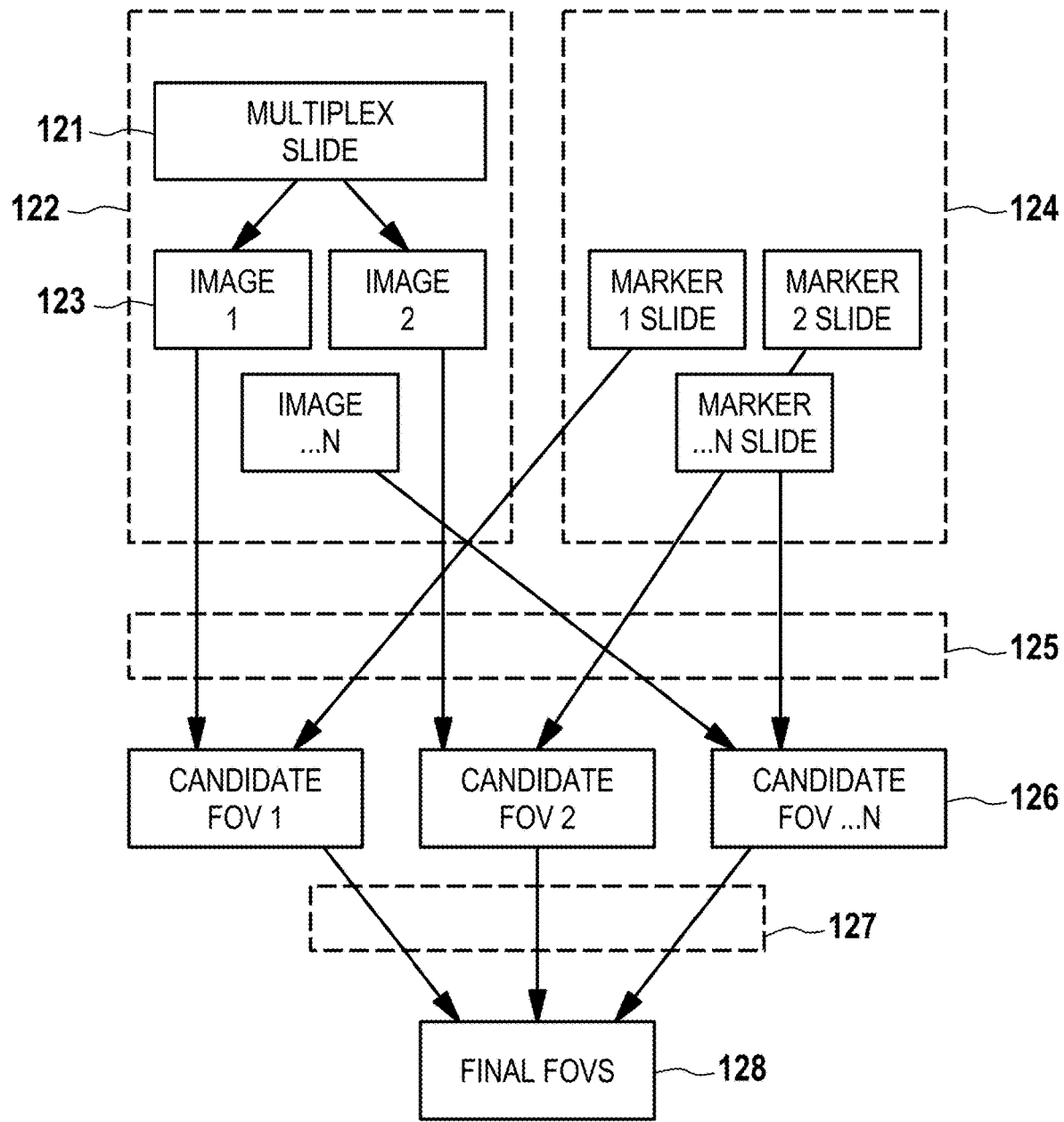

FIGS. 1A-1B respectively depict a system 100 and a workflow for automatic FOV selection, according to an exemplary embodiment of the present subject disclosure. Referring to FIG. 1A, a system 100 comprises a memory 110, which stores a plurality of processing modules or logical instructions that are executed by processor 105 coupled to computer 101. An input from image acquisition system 102 may trigger the execution of one or more of the plurality of processing modules. Besides processor 105 and memory 110, computer 101 also includes user input and output devices such as a keyboard, mouse, stylus, and a display/touchscreen. As will be explained in the following discussion, processor 105 executes logical instructions stored on memory 110, including automatically identifying one or more FOVs in an image of a slide (containing a biological specimen, such as a tissue sample) that has been stained with one or more stains (for example, fluorophores, quantum dots, reagents, tyramides, DAPI, etc.).

Image acquisition system 102 may include a detector system, such as a CCD detection system, or a scanner or camera such as a spectral camera, or a camera on a microscope or a whole-slide scanner having a microscope and/or imaging components (the image acquisition system is not limited to the aforementioned examples). For example, a scanner may scan the biological specimen (which may be placed on a substrate such as a slide), and the image may be saved in a memory of the system as a digitized image. Input information received from image acquisition system 102 may include information about a target tissue type or object, as well as an identification of a staining and/or imaging platform. For instance, the sample may have been stained by means of application of a staining assay containing one or more different biomarkers associated with chromogenic stains for brightfield imaging or fluorophores for fluorescence imaging. Staining assays can use chromogenic stains for brightfield imaging, organic fluorophores, quantum dots, or organic fluorophores together with quantum dots for fluorescence imaging, or any other combination of stains, biomarkers, and viewing or imaging devices. Moreover, a typical sample is processed in an automated staining/assay platform that applies a staining assay to the sample, resulting in a stained sample. Input information may further include which and how many specific antibody molecules bind to certain binding sites or targets on the tissue, such as a tumor marker or a biomarker of specific immune cells. The choice of biomarkers and/or targets may be input into the system, enabling a determination of an optimal combination of stains to be applied to the assay. Additional information input into system 100 may include any information related to the staining platform, including a concentration of chemicals used in staining, a reaction times for chemicals applied to the tissue in staining, and/or pre-analytic conditions of the tissue, such as a tissue age, a fixation method, a duration, how the sample was embedded, cut, etc. Image data and other input information may be transmitted directly or may be provided via a network, or via a user operating computer 101.

An unmixing module 111 may be executed to unmix the image, for instance if the image is a multiplex image. Unmixing module 111 unmixes the image into individual marker color channels. Unmixing module 111 may read from a reference color matrix database 112 to obtain the reference color matrix and use the reference color matrix to perform unmixing operations. If the image is of a single stain slide, the image can be directly used for FOV selection. In either case, a heat map computation module 113 may be executed to evaluate a heat map for each individual marker image, or single stain image. A heat map maps the density of various structures or biomarkers on the whole-slide image. To accomplish this, heat map computation module 113 may perform operations such as assigning colors to a low pass filtered image that is processed by low pass filter module 114. A tissue region mask may also be applied to the low pass filtered image. The heat map illustrates pixels according to the respective densities of the pixels, and thus, corresponds to the density of the cell distribution in each image. For example, the heat map will distinguish high-density pixels from low-density pixels by illustrating higher density pixels in a color that is warmer than a color used for lower density pixels. Local max filter module 115 may be executed to apply a local max filter to the low pass filtered image to obtain the local maxima of the image. Subsequently, a top K FOV selection module 116 may be executed to select the top K regions with the highest densities from the local max filtered image. The top K regions are designated as the candidate FOVs for each image. For example, the cells may be clustered together in the high-density region while they are more scattered in the low-density region. The FOVs from each image are merged together by merge FOV module 117, which performs operations such as taking all the FOVs or the FOVs from selected markers only and merging them. A registration module 118 is invoked to transfer all the images to the same coordinate system, so that the coordinates of the FOVs can be directly added up in the same coordinate system.

As described above, the modules include logic that is executed by processor 105. "Logic", as used herein and throughout this disclosure, refers to any information having the form of instruction signals and/or data that may be applied to affect the operation of a processor. Software is one example of such logic. Examples of processors are computer processors (processing units), microprocessors, digital signal processors, controllers and microcontrollers, etc. Logic may be formed from signals stored on a computer-readable medium such as memory 110 that, in an exemplary embodiment, may be a random access memory (RAM), read-only memories (ROM), erasable/electrically erasable programmable read-only memories (EPROMS/EEPROMS), flash memories, etc. Logic may also comprise digital and/or analog hardware circuits, for example, hardware circuits comprising logical AND, OR, XOR, NAND, NOR, and other logical operations. Logic may be formed from combinations of software and hardware. On a network, logic may be programmed on a server, or a complex of servers. A particular logic unit is not limited to a single logical location on the network. Moreover, the modules need not be executed in any specific order. Each module may call another module when needed to be executed.

An exemplary workflow for FOV selection is depicted in FIG. 1B. In FIG. 1B, N represents the number of markers applied to the slides. For a multiplex slide 121, color unmixing 122 is performed, for example according to the unmixing method disclosed in Patent Application 61/830, 620, filed Jun. 3, 2013, and WO 2014/195193 A1 entitled "Image Adaptive Physiologically Plausible Color Separation", the disclosure of which is hereby incorporated by reference in its entirety. The method disclosed in Patent Application 61/943,265, filed Feb. 21, 2014, and entitled. "Group Sparsity Model for Image Unmixing", and PCT/EP2014/078392 filed 18 Dec. 2014 which is hereby incorporated by reference in its entirety, is, in an exemplary embodiment utilized to obtain an image 123 for each marker. Otherwise, if the image is a single stain slide, scanned images 124 of single stain slides for each marker are utilized as an input to an automatic FOV selection system, such as the system depicted in FIG. 1A. For example, a heat map computation operation may be performed to compute the hotspot 125 from the image of each marker to generate the top candidate FOVs 126 for each marker. The candidate FOVs 126 may be integrated 127 to generate the final FOV list 128. Final FOV list 128 comprises a list of possible FOVs for selection by a pathologist to utilize for evaluating the biological specimen, for example, immune cells.

As used herein and throughout this disclosure, hotspots are regions containing a high density of marked (i.e., stained) cells, for example hotspots can be cells from different types of images and markers such as ISH, IHC, fluorescent, quantum dots etc. The subject disclosure uses immune cells in an IHC image as an example to demonstrate this feature (as previously discussed, the present invention is not limited to immune cells in an IHC image). In light of the subject disclosure, various algorithms may be used by those having ordinary skill in the art to find hotspots and to use automatic hotspot selection as a module in immunoscore computation. Exemplary embodiments of the subject disclosure utilize the automatic FOV selection operations described herein to solve the problem of avoiding biased manually selected FOVs. To automatically identify FOVs that may be of interest to a pathologist or other evaluator, a heat map is computed for each marker or image representing a single marker, based on a low-resolution image (e.g. a 5× zoom image).

Figure 2:
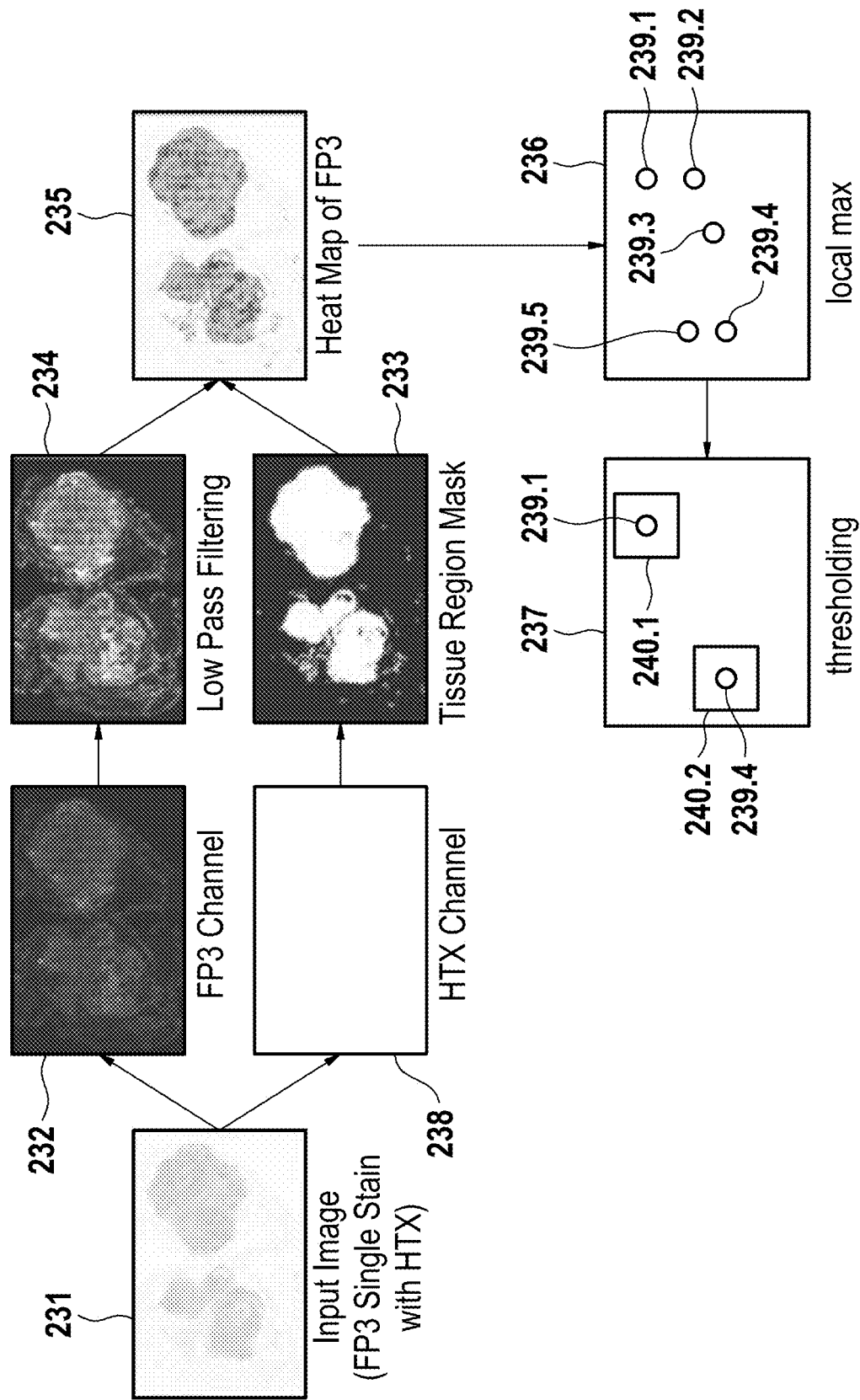
FIG. 2 depicts a heat map computation, according to an exemplary embodiment of the present subject disclosure.

FIG. 2 depicts a heat map computation, according to an exemplary embodiment of the present subject disclosure. The operations described in FIG. 2 illustrate how a heat map computation is utilized to identify hotspots. For example, given a single-marker channel 232 of an input image 231, a low-pass-filtered image 234 is used to generate heat map 235, which basically takes the low pass filtered image 234 as input and applies a color map on top of it for visualization purposes. For example, a red color may correspond to high intensity pixels in the low pass filtered image and a blue color may correspond to low intensity pixels. Other depictions of color and/or intensity may be evident to those having ordinary skill in the art in light of this disclosure. A tissue region mask 233 may be created by identifying the tissue regions and excluding the background regions. This identification may be enabled by image analysis operations such as edge detection, etc. Tissue region mask 233 is used to remove the non-tissue background noise in the image, for example the non-tissue regions.

In the embodiment considered with respect to FIG. 2 the input image 231 is stained by means of a stain and its respective counter-stain which provides two channels, namely the FP3 channel and the HTX channel. The two-channel image 231 is unmixed which provides the unmixed images 232 and 238 of the FP3 and HTX channels, respectively.

The unmixed image 232 is then low pass filtered by means of a spatial low pass filter which provides the low pass filtered image 234. Next, the heat map 235 may be added to the low pass filtered image 234 for visualization purposes.

Figure 3:
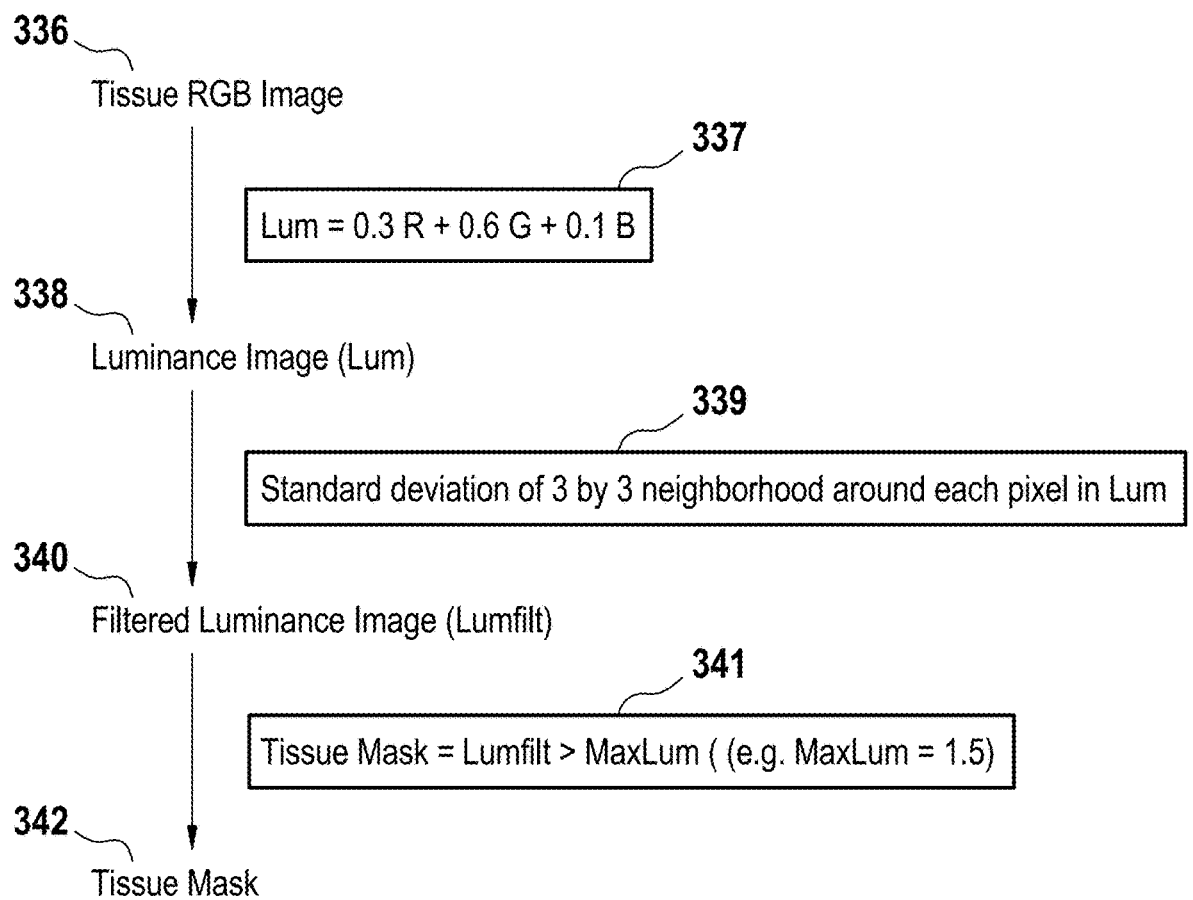
FIG. 3 depicts a tissue mask computation, according to an exemplary embodiment of the subject disclosure.

The unmixed image 238 is then used to compute the tissue region mask 233 by the method described in FIG. 3.

The low pass filtered image 234 with or without the added heat map 235 is then local maximum filtered which provides the local max filtered image 236. The local max filtered image 236 comprises a number of local maxima 239, in the example considered here five local maxima 239.1-239.5 as depicted in FIG. 2. Next, a thresholding operation is performed on the local max filtered image 236 such as by applying a threshold onto the local max filtered image 236 such that only the local maxima 239.1 and 239.4 that surpass this threshold are not removed by the thresholding operation.

Alternatively the local maxima 239 are ranked in a sorted list and only a number of the K topmost local maxima are taken from the list, where K is 2 for explanatory purposes in the embodiment considered here, resulting in the local maxima 239.1 and 239.4. Each of the local maxima 239 consists of a set of neighboring pixels.

This thresholding operation provides the thresholded image 237. Each of the local maxima 239.1 and 239.4 in the thresholded image 237 may define the location of a respective field of view 240.1 and 240.2, respectively. Depending on the implementation, these fields of view 240.1 and 240.2 may be candidate fields of view for testing whether these fields of view can be merged with other fields of view in subsequent processing operations as described below with respect to FIG. 6. The positions of the fields of view 240.1 and 240.2 are defined by means of the thresholded image 237 and its local maxima. However, the content of the fields of view is taken from the respective image area within the original multi-channel image 231 in order to take advantage of the full pictorial information content for performing an image analysis of the respective field of view.

FIG. 3 depicts a tissue mask computation, according to an exemplary embodiment of the subject disclosure, such as to compute tissue mask 233 from unmixed image 238 by means of a segmentation technique. A linear combination 337 of the RGB channels 336 of the tissue RGB image is computed to create a grayscale luminance image 338. The combination weights for the R, G and B channels (e.g. 0.3, 0.6, 0.1 in 337) are subject to change based on different applications. A 3 pixel by 3 pixel standard deviation filter 339 is applied to the luminance image 338, resulting in a filtered luminance image 340. Here the filter size (e.g. 3 by 3, 5 by 5) is subject to change based on different applications. The tissue mask 342 is a binary image obtained from thresholding 341 the filtered luminance image 340. For example, tissue mask 342 may comprise regions with pixel intensity value larger than 1.5. The thresholding parameter MaxLum (e.g. 1.5, 2.0, 3.0) can vary based on different applications.

Figure 4:
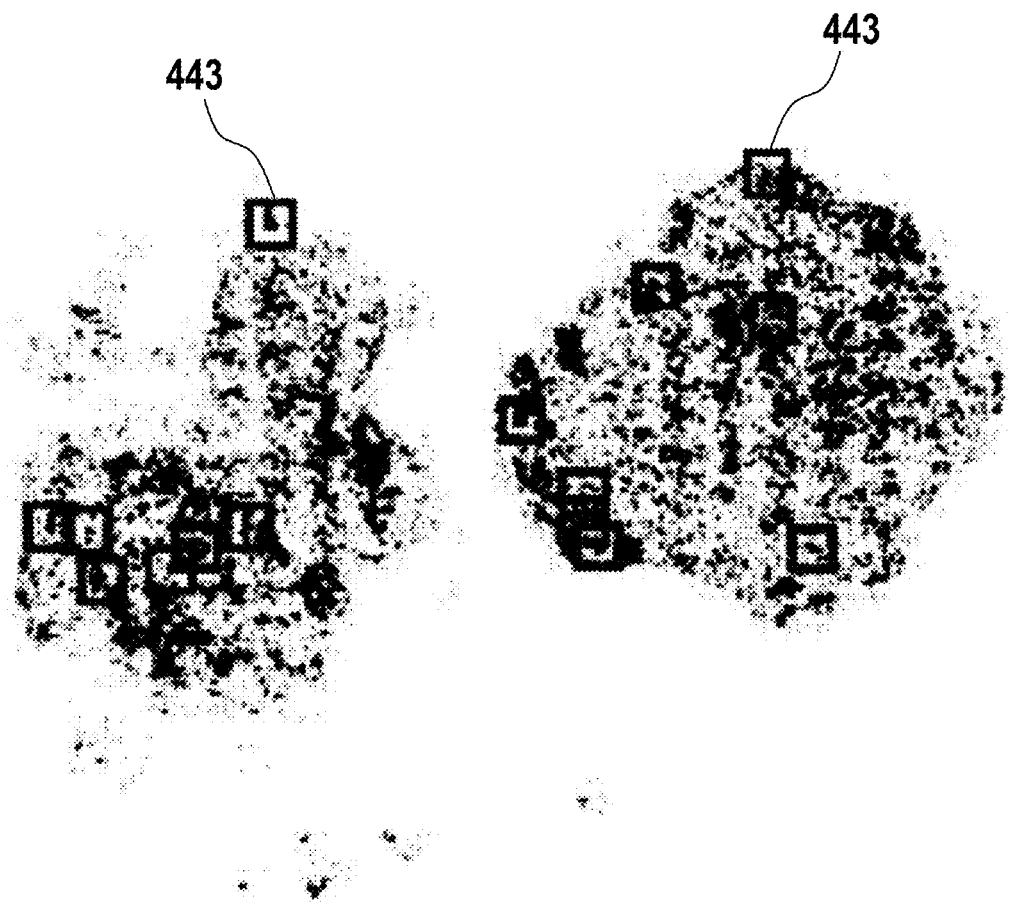
FIG. 4 depicts candidate FOVs, according to an exemplary embodiment of the subject disclosure.

FIG. 4 depicts candidate FOVs, according to an exemplary embodiment of the subject disclosure. Candidate FOVs 443 are selected from the top K highest density regions (also called hot spots) of the heat map. For example, K can be chosen from 5, 10, 15, 20 etc. A local maximum filter is applied to the low pass filtered image 234 with the added heat map 235 (cf. FIG. 2) in order to provide a local max filtered image. 236 It is to be noted that the heat map 235 is not essential for the processing but serves for visualization purposes. A local maximum filter is a function to identify a constant value connected region of pixels with the external boundary pixels all having a lower value. It can use 4 or 8 connected neighborhoods for 2-D images. The implementation of this functionality is available at Matlab (http://www.mathworks.com/help/images/ref/imregional-max.html).

The local maximum is obtained as the average intensity with in the connected region. The local maximum values are sorted providing a sorted list to produce the rank of the hotspots and top K hotspots are reported thus thresholding the local max filtered image. Alternatively a predefined threshold is applied on the local maximum filtered image such that all hotspots above the threshold are reported. The regions returned by the local maximum filter computation module are the locations of the local maximums.

As described herein, different FOVs may be obtained for different marker images resulting from unmixing of a multiplex slide or from single stain slides. The FOVs are integrated to ensure that for each patient under diagnosis, the same set of FOVs is referenced across different markers. There are several possible options to integrate FOVs. FIGS. 5A-5B depict merging of FOVs from all markers and from selected markers, respectively, according to an exemplary embodiment of the subject disclosure. For example, all candidate FOVs from the different marker images may be merged, as depicted in FIG. 5A. In the alternative, different FOVs for different marker images may be selected and merged, as depicted in FIG. 5B.

Figure 6A:
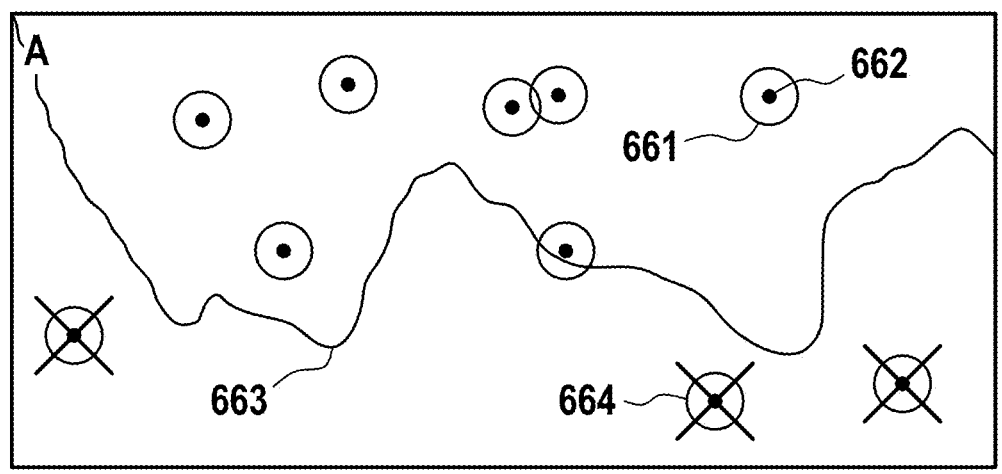
FIGS. 6A-6C depict integrating FOVs, according to exemplary embodiments of the subject disclosure.
Figure 6B:
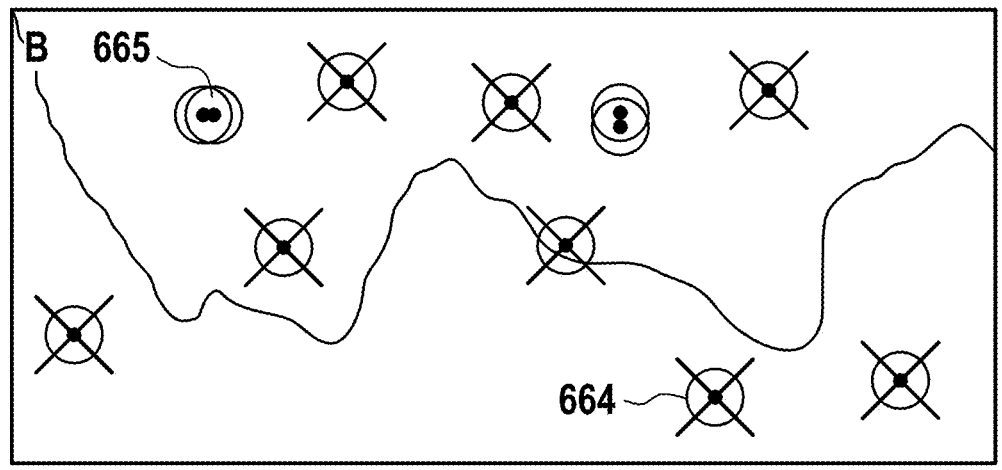

Moreover, different FOVs for different marker images may be analyzed independently based on a user's needs. FIGS. 6A-6B depict integrating FOVs, according to an exemplary embodiment of the subject disclosure. With reference to FIG. 6A, all the FOVs are selected and, with reference to FIG. 6B, only the FOVs corresponding to specific markers are selected. Each circle 661 represents a possible FOV for the markers. Each dot 662 in each circle 661 represents a local maximum point for each FOV. Each circle 661 may surround a different marker. Line 663 corresponds to the separation between the tumor and the non-tumor regions. FOVs 664 outside of tumor regions are excluded by morphological operations, such as union and intersection. The final FOVs (i.e., the FOVs that are selected for analysis) are the union of all the FOVs from each marker, as depicted by the methods of FIGS. 5A and 5B.

In some embodiments, the FOV may be a rectangle about the local maxima. In other embodiments, the FOV may be an arbitrary shape. In some embodiments, the FOV may be a border around a region of high intensity.

Figure 6C:
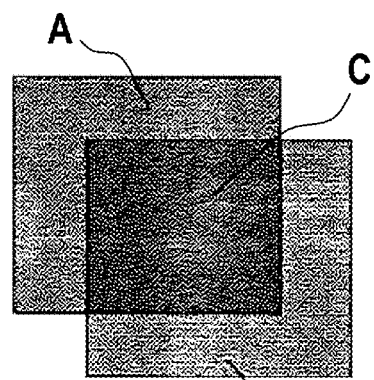

FIG. 6B depicts specifying the most important markers for a given problem by the user, and merging the FOVs based on the selected markers. For example, assume PF3 and CD8 are the most important markers. All the images of single markers may be aligned to the same coordinate system (e.g. the reference coordinate can be the slide section in the middle of the tissue block or the slide with a specific marker) using image registration. Each image may therefore be aligned from its old coordinate system to the new reference coordinate system. FOVs of selected markers (e.g. FP3 and CD8) from an individual marker image may be aligned to the common space and merged using morphological operations such as union and intersection to obtain the merged FOVs (FOVs 665 in FIG. 6B). FIG. 6C shows the morphological operations. Assume A is the FOV from CD8 image and B is the FOV from FP3 image. We first overlay A and B in the same coordinate system and obtain the overlapped region C by computing the intersection of A and B. We then evaluate the ratio of the area of C and the area of A (or B). If the ratio is greater than a threshold (e.g. 0.6, 0.8, etc.), we select the FOVs, otherwise we discard the FOVs. The merged FOVs may be mapped back to all the single marker images using inverse registration (i.e. align the registered image in the new coordinate system back to its original old coordinate system) for further analysis. FOVs 664 outside tumor regions are excluded.

Figure 7:
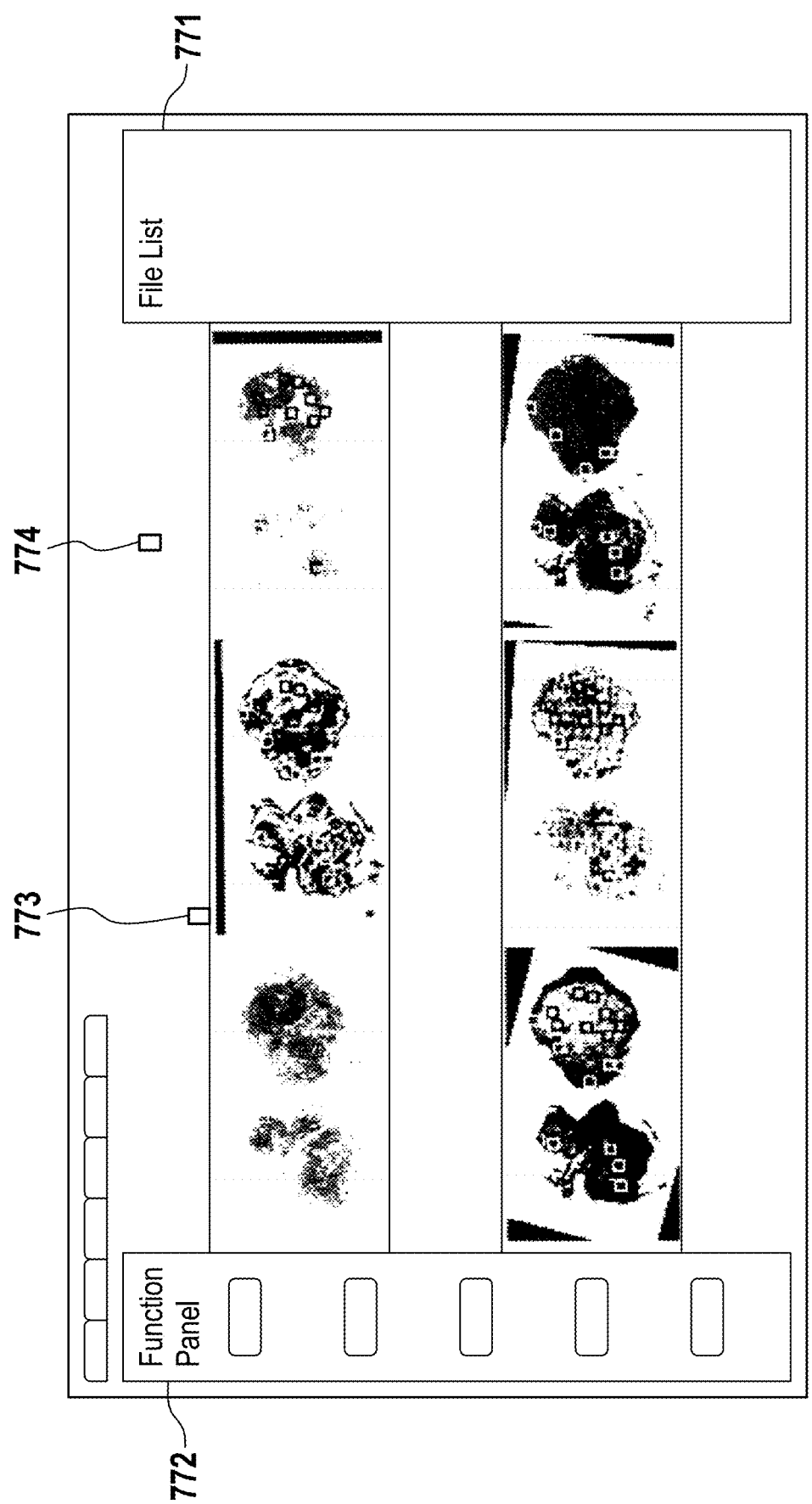
FIG. 7 depicts a user interface for image analysis using an all marker view, according to an exemplary embodiment of the subject disclosure.
Figure 8:
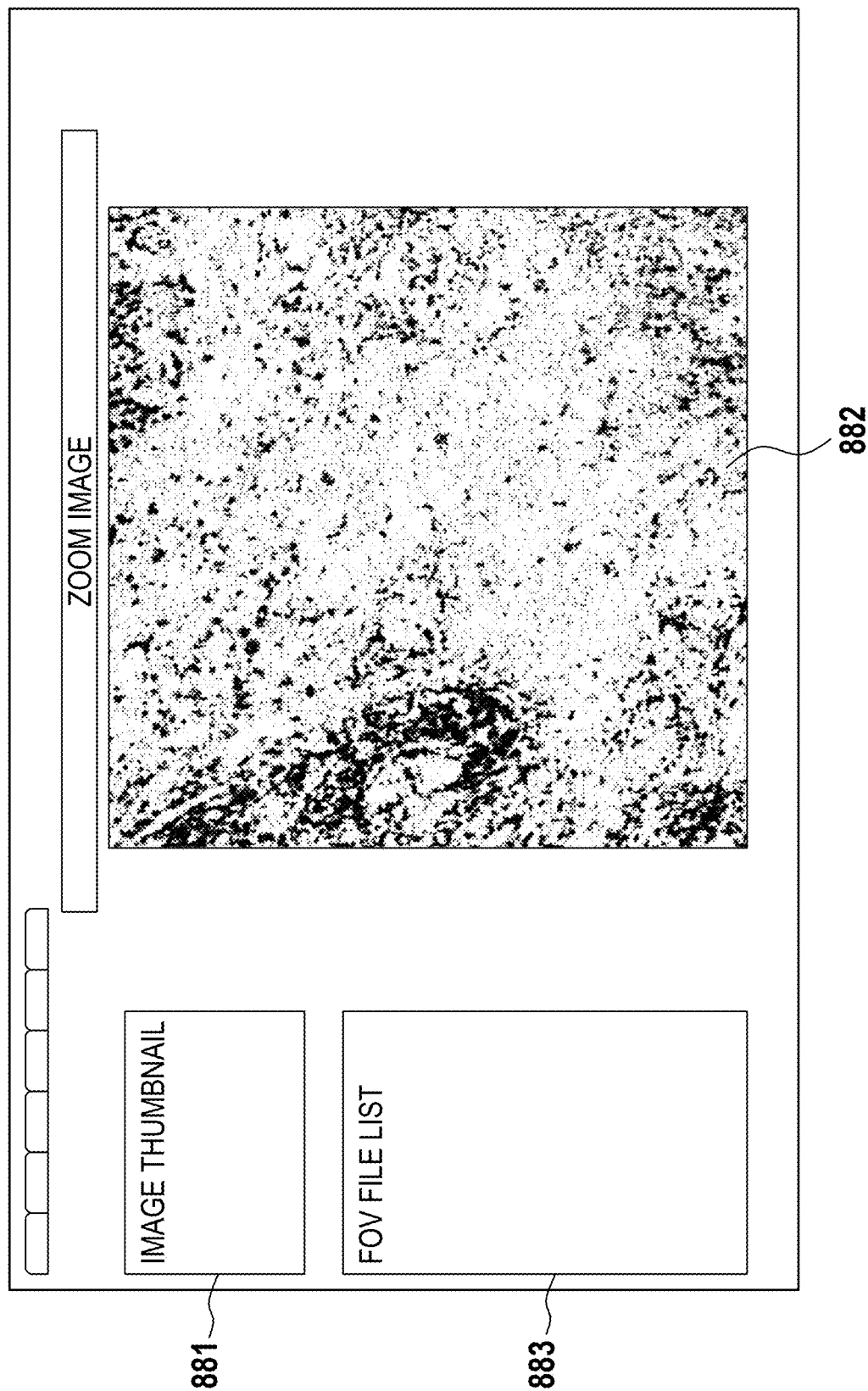
FIG. 8 depicts a user interface for image analysis using an individual marker view, according to an exemplary embodiment of the subject disclosure.

FIGS. 7 and 8 depict user interfaces for image analysis using all marker views and individual markers views, according to exemplary embodiments of the subject disclosure. In these exemplary embodiments, a user interface associated with a computing device may be utilized to perform the FOV selection. The user interface may have All Marker functionalities (FIG. 7) and Single Marker Functionalities (FIG. 8). The marker functions can be accessed by selecting from a tab on the top of the user interface. When using the All Marker function as shown in FIG. 7, all the markers may be viewed and the heat map computation, FOV selection, key marker selection, registration and inverse registration can be performed. In the All Marker View (i.e., a view that illustrates all the markers side by side) options may be provided such as loading a list 771 of image folders(a) with each folder containing all the images including the multiplex and single stains for the same case. Allow batch processing of all the images in the list. Other options provided in a feature panel 772 may include linking the axes for all the images to simultaneously zoom in and out on the images to view the corresponding regions (b), selecting the number of FOVs(c), align the images to a common coordinate system(d), and allowing the user to pick the most important markers for integrating FOVs(e). Colors may be depicted indicating the markers that the FOVs come from. Further options provided may include allowing the user to switch 774 between the heat map view and IHC view, and computing 773 the heat map of each image.

FIG. 8 depicts the Individual Marker View or Single Marker View, displaying the final selected FOVs for each marker. Features provided in this view may include displaying a thumbnail 881 of the whole slide image, with the FOVs annotated by box in the thumbnail image and a text number near the box indicating the index of the FOV. Other features may include allowing the user to select from the FOV list 883 to delete un-wanted FOVs using checkbox, displaying the high resolution image of the selected FOV 882, saving the image of each FOV into a local folder at original resolution (d), and allowing the user to assign a label to each FOV (e). The labels can be the regions associated with the FOV such as peripheral region, tumor region, and lymphocyte region etc. It will be recognized by those having ordinary skill in the art that these exemplary interfaces may differ from application to application and across various computing technologies, and may use different versions of interface so long as the novel features described herein are enabled in light of this disclosure.

Therefore, the systems and methods disclosed herein provide automatic FOV selection, and have been found important to analyzing biological specimens, and useful in computing tissue analyses scores, for example in immunoscore computations. Operations disclosed herein overcome disadvantages known in the prior art, such as FOV selection being un-reproducible and biased in human reader manual FOV selection, as the automatic FOV selection is able to provide the FOVs via a computer without relying on a human reader's manual selection. When combined with automatic immune cell counting and data analysis, the disclosed operations allow a complete automatic workflow that takes in one or more scanned images or image data as input, and outputs the final clinical outcome prediction. The systems and methods disclosed herein provide automatic FOV selection, and have been found important to analyzing biological specimens, and useful in computing tissue analyses scores, for example in immunoscore computations. Operations disclosed herein overcome disadvantages known in the prior art, such as FOV selection being un-reproducible and biased in human reader manual FOV selection, as the automatic FOV selection is able to provide the FOVs via a computer without relying on a human reader's manual selection. When combined with automatic immune cell counting and data analysis, the disclosed operations allow a complete automatic workflow that takes in one or more scanned images or image data as input, and outputs the final clinical outcome prediction.

Figure 9:
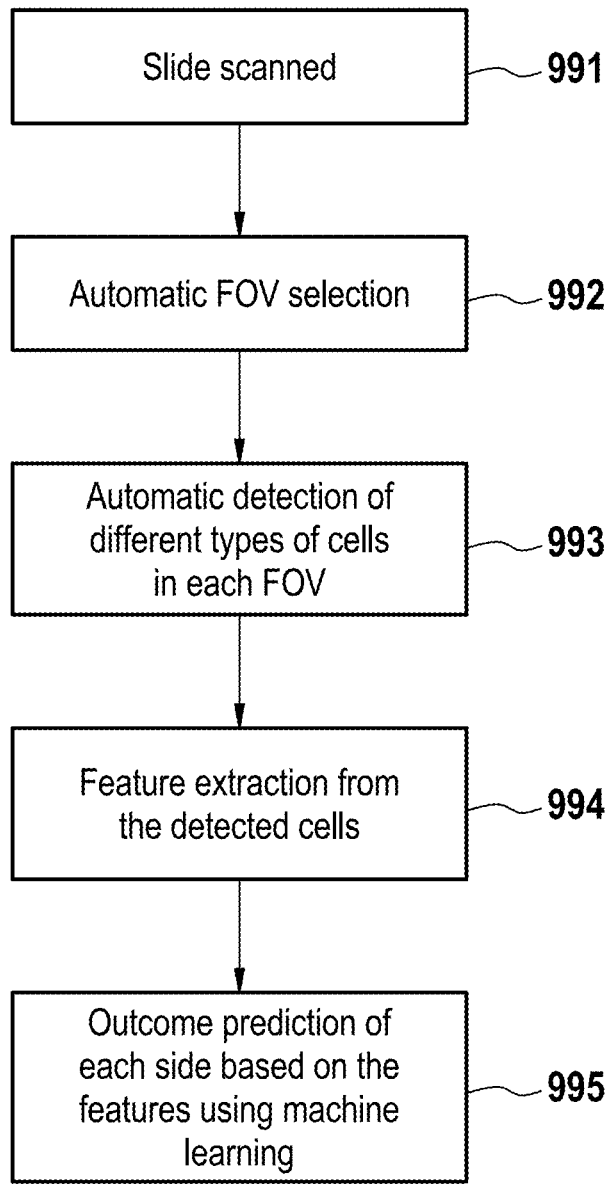
FIG. 9 depicts a digital pathology workflow for immunoscore computation, according to an exemplary embodiment of the subject disclosure.

FIG. 9 depicts a digital pathology workflow for immunoscore computation, according to an exemplary embodiment of the subject disclosure. This embodiment illustrates how the automatic FOV selection method disclosed herein may be utilized in an immunoscore computation workflow. For example, after a slide is scanned 991 and the FOVs have been selected 992 according to the operations disclosed herein, an automatic detection 993 of different types of cells in each FOV can be performed. The automatic cell detection technique, for example, according to the method disclosed in U.S. Patent Application Ser. No. 62/002,633 filed May 23, 2014 and PCT/EP2015/061226, entitled "Deep Learning for Cell Detection", which is hereby incorporated by reference in its entirety, is an exemplary embodiment utilized to obtain detect the cells. Further, features (e.g., features related to the number and/or types of cells identified) can be extracted 994 that are related the one or more cells detected for each biological specimen (e.g., tissue samples, etc.). The features can be number of different types of cells and the ratios of cells in different FOVs related to different regions in the tissue image such as the tumor region and the periphery region. Those features can be used to train 995 a classifier (such as Random Forest and Support Vector Machine) and classify each case to the different outcome classes (e.g., likelihood of relapse or not).

Figure 10:
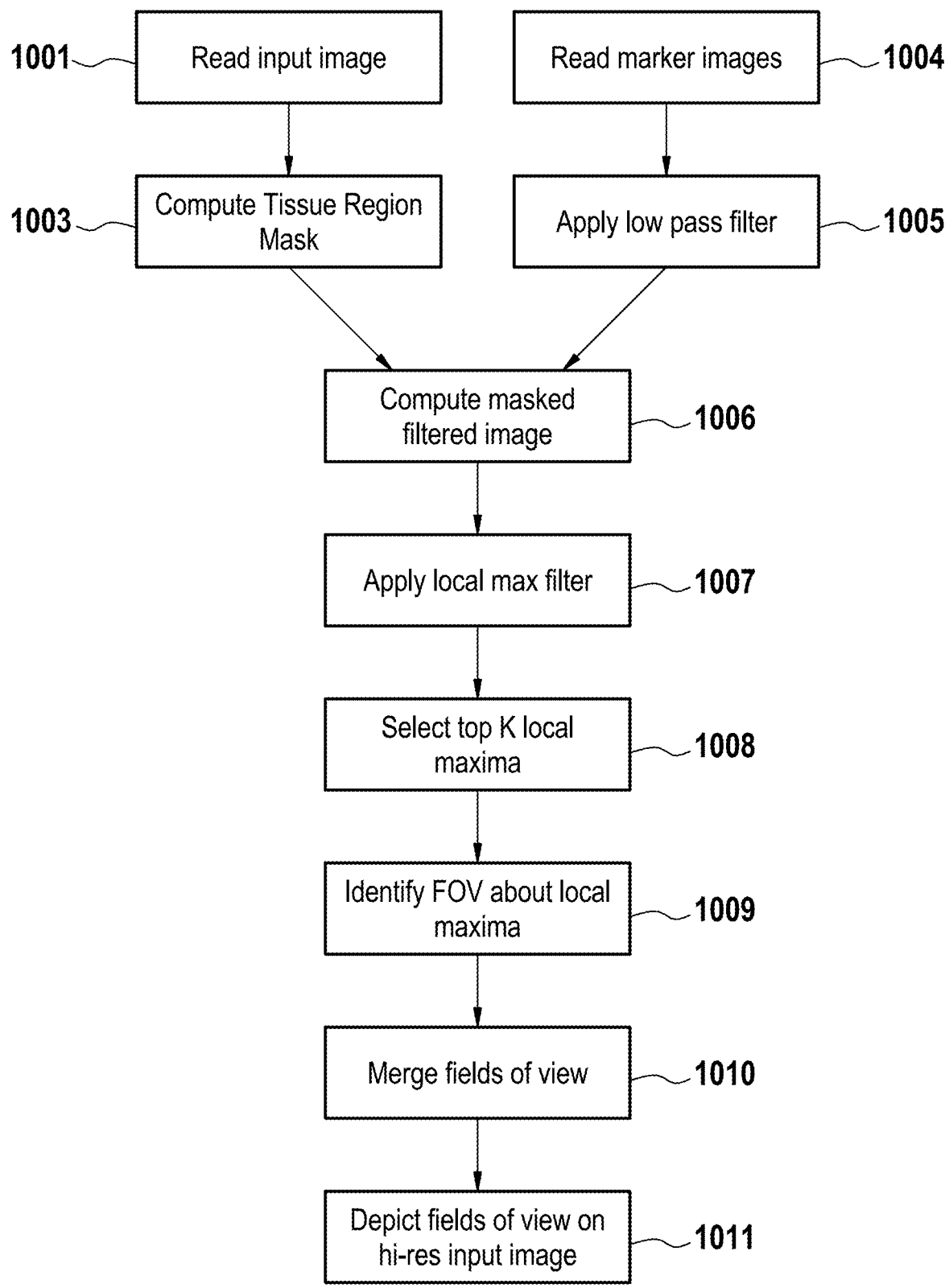
FIG. 10 depicts a process flow chart for an exemplary embodiment of the present invention.

FIG. 10 depicts a process flow for an exemplary embodiment of the present invention. An input image (1001) is received from the image acquisition system. In addition, a series of low-resolution marker images (1004) are received from the image acquisition system. The marker images may be derived by unmixing of the high-resolution image or may be received as single stain slide images. The low resolution input image is used to compute a tissue region mask (1003), which indicates which parts of the image contain tissue of interest. The low resolution image marker images are passed through a low pass filter to produce filtered image marker images (1005). The tissue region mask is then applied to the low pass filtered images to block out (reduce to 0) regions that are not of interest. The results in a masked filtered image (1006) for each marker. A local max filter is applied to a max filtered image to identify local maxima (1007). The top K local maxima are selected (1008), and for each local maxima a field of view is defined (1009). Then the FOVs for each image are merged (1010), by transferring all images to a common coordinate frame and overlaying and combining any overlapping fields of view. The merged fields of view are then transferred back to the original image coordinate system, extracting the regions from the high resolution input image for analysis.

Figure 11A:
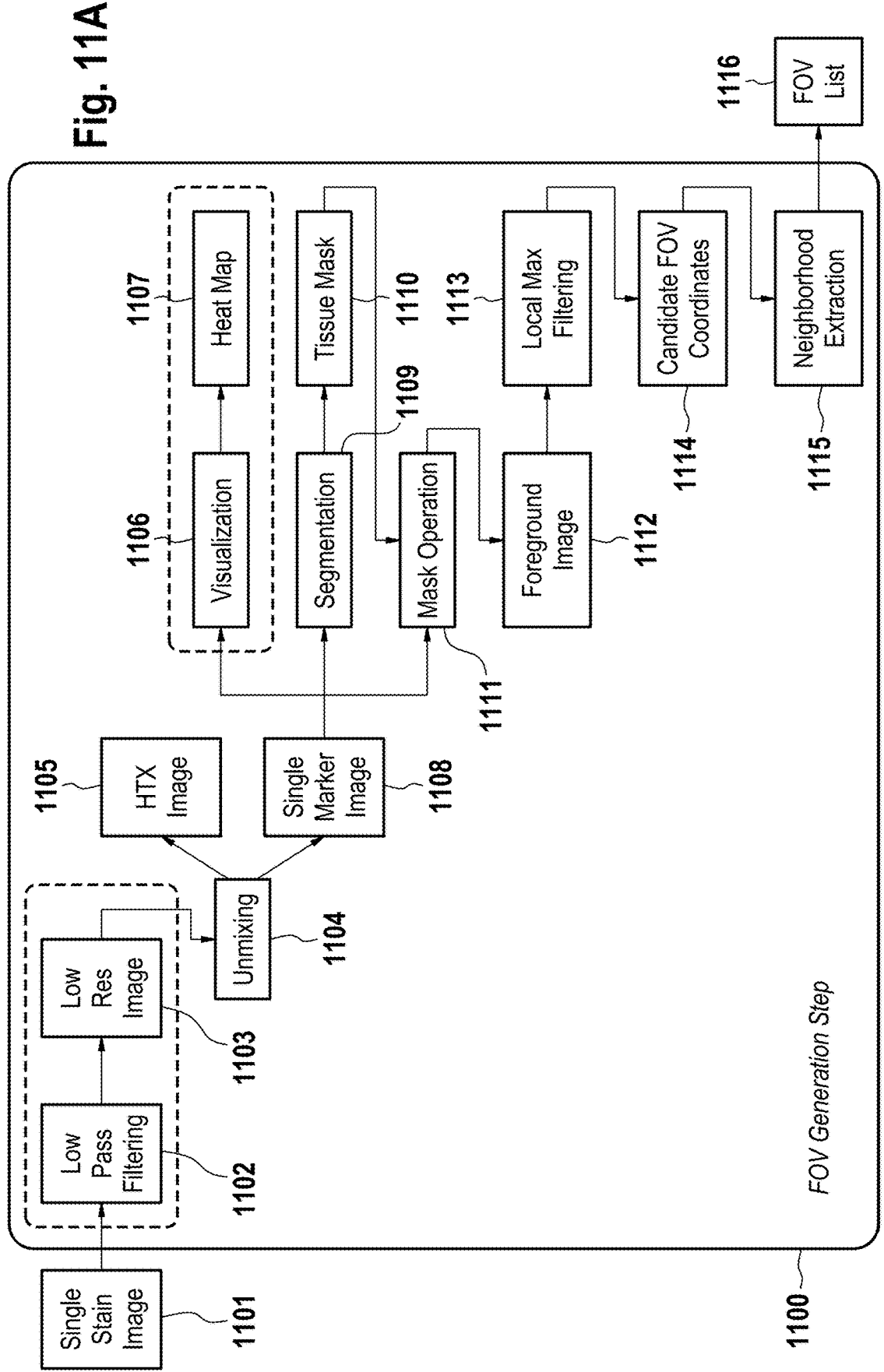
FIGS. 11a and 11b depicts a process flow chart for an exemplary embodiment of the present invention starting with single-stain marker images.
Figure 11B:
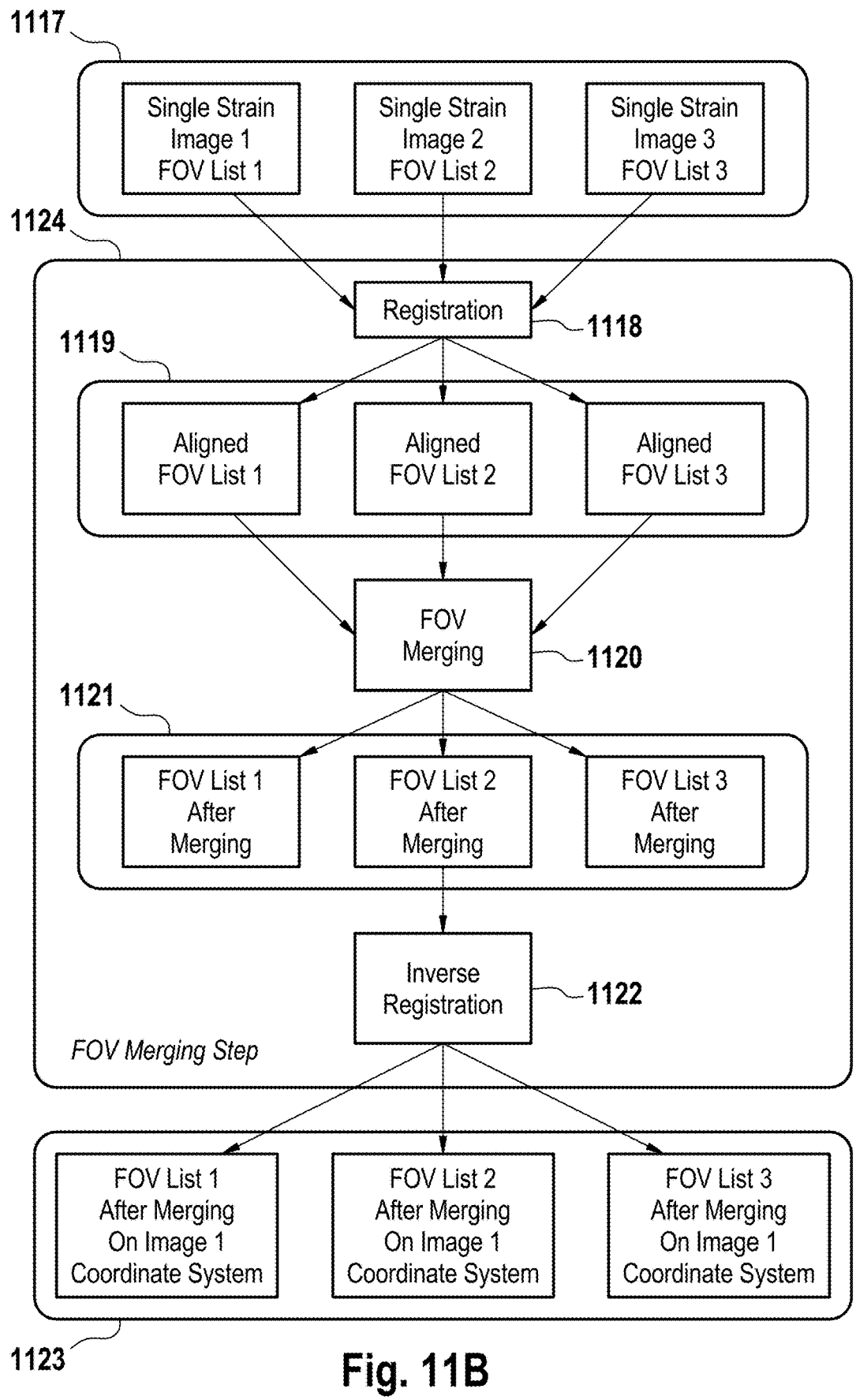

FIG. 11 shows a different process flow for another exemplary embodiment of the present invention. The process flow is divided into a FOV generation step (1100) as shown in FIG. 11a, and a field of view merging step (1124) as shown in FIG. 11b. In the FOV generation step, single stain images (1101) are received from the image acquisition system. The images are low-pass filtered (1102). In some embodiments, the images may be converted to a lower resolution (1103), which speeds processing. In some embodiments an unmixing step (1104) may be applied to extract the color channel of interest from the single stain slides, if it is not already reduced to a single color channel, producing single marker images (1108). In some embodiments an HTX image (1105) may also be generated. The single marker image is then segmented (1109) to identify features of interest. From the segmented image a tissue region mask (1110) is generated. In some embodiments, the single marker image may be visualized (1106) using a heat map (1107), by assigning colors to regions of varying intensity in the single marker image. The tissue region mask (1110) is then applied to the single marker image (1111), resulting in a foreground image (1112), which displays the intensity of the marker image only in the tissue region of interest. The foreground image is passed through a local max filter (1113), to identify peaks in intensity. Candidate FOV coordinates are identified as the top K peaks of the local max filtered image (1114). Finally, regions around each candidate FOV coordinate are defined (1115) to obtain the list of candidate FOVs (1116). These operations are performed for each single stain slide.

In the FOV merging step (1124), all of the candidate FOV lists for the various single stain slides are obtained (1117). The images are registered to a single coordinate frame (1118), by selecting one image as a reference image and transforming the other images to match the reference image. The candidate FOV coordinates are then transformed accordingly to obtain aligned candidate FOV lists (1119). The FOVs are then overlaid and merged (1120), to obtain a unified FOV list for all images (1121). Inverse registration is then performed (1122) to transform the unified FOVs back to each of the original coordinate systems of the original single stain images (1123). The FOVs can then be displayed on the original single stain slides.

Figure 12:
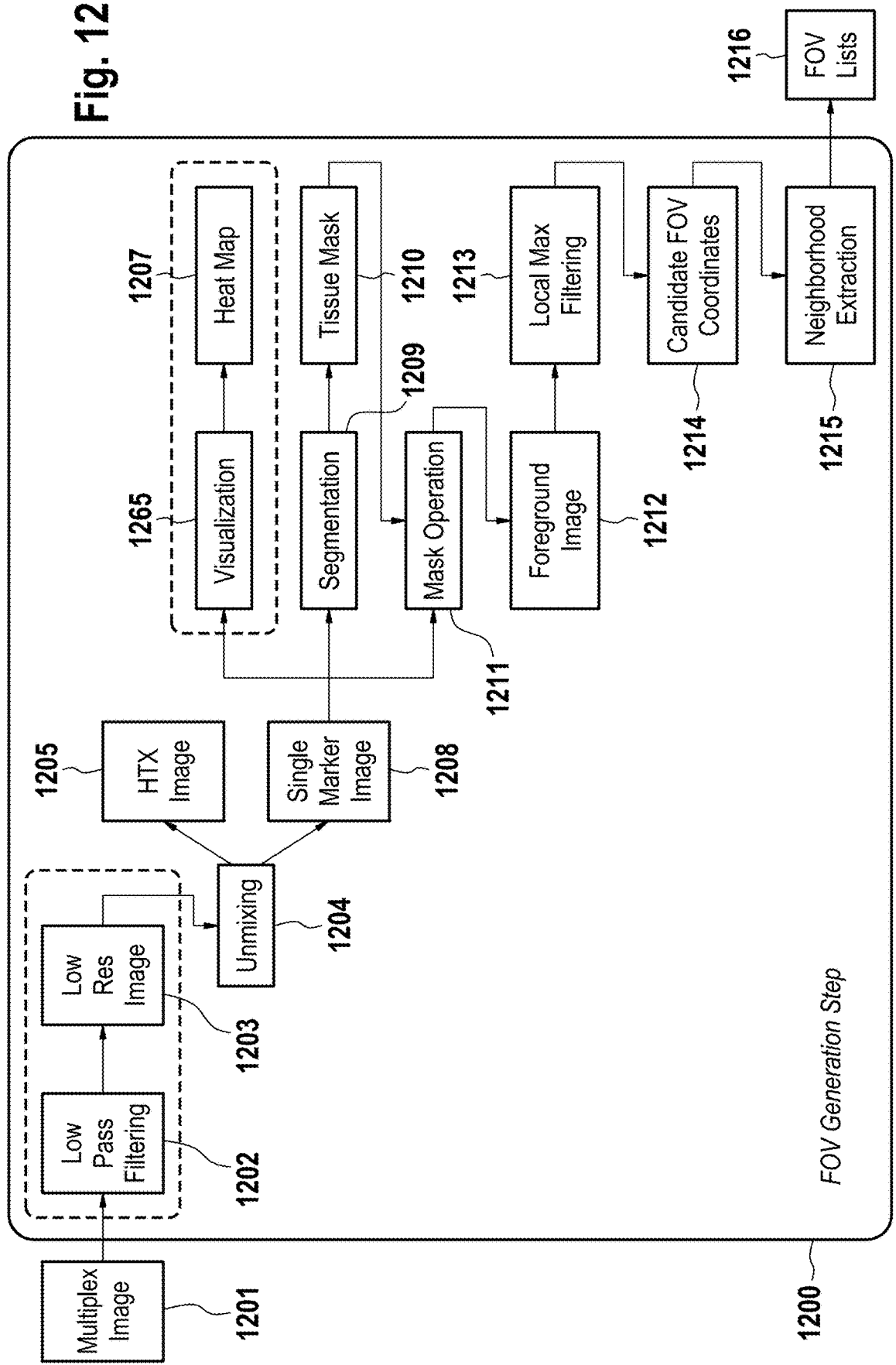
FIG. 12 depicts a process flow chart for an exemplary embodiment of the present invention starting with a multiplex slide.

FIG. 12 shows process flow of an alternative embodiment of the present invention, using multiplex slides as inputs (1201). In the FOV generation step, multiplex slides (1201) are received from the image acquisition system. The images are low-pass filtered (1202). In some embodiments, the images may be converted to a lower resolution (1203), which speeds processing. In this embodiment, an unmixing step (1204) is applied to extract the color channels of interest from the multiplex slide, producing a plurality of single marker images (1208). In some embodiments an HTX image (1205) may also be generated. The first single marker image is then segmented (1209) to identify features of interest. From the segmented image a tissue region mask (1210) is generated. In some embodiments, the single marker image may be visualized (1265) using a heat map (1207), by assigning colors to regions of varying intensity in the single marker image. The tissue region mask (1210) is then applied to the single marker image (1210), resulting in a foreground image (1212) which displays the intensity of the marker image only in the tissue region of interest. The foreground image is passed through a local max filter (1213), to identify peaks in intensity. Candidate FOV coordinates are identified as the top K peaks of the local max filtered image (1214). Finally, regions around each candidate FOV coordinate are defined (1215) to obtain the list of candidate FOVs (1216). These operations are performed for each single stain slide in order. The FOV merging step proceeds as in FIG. 11b.

Figure 13:
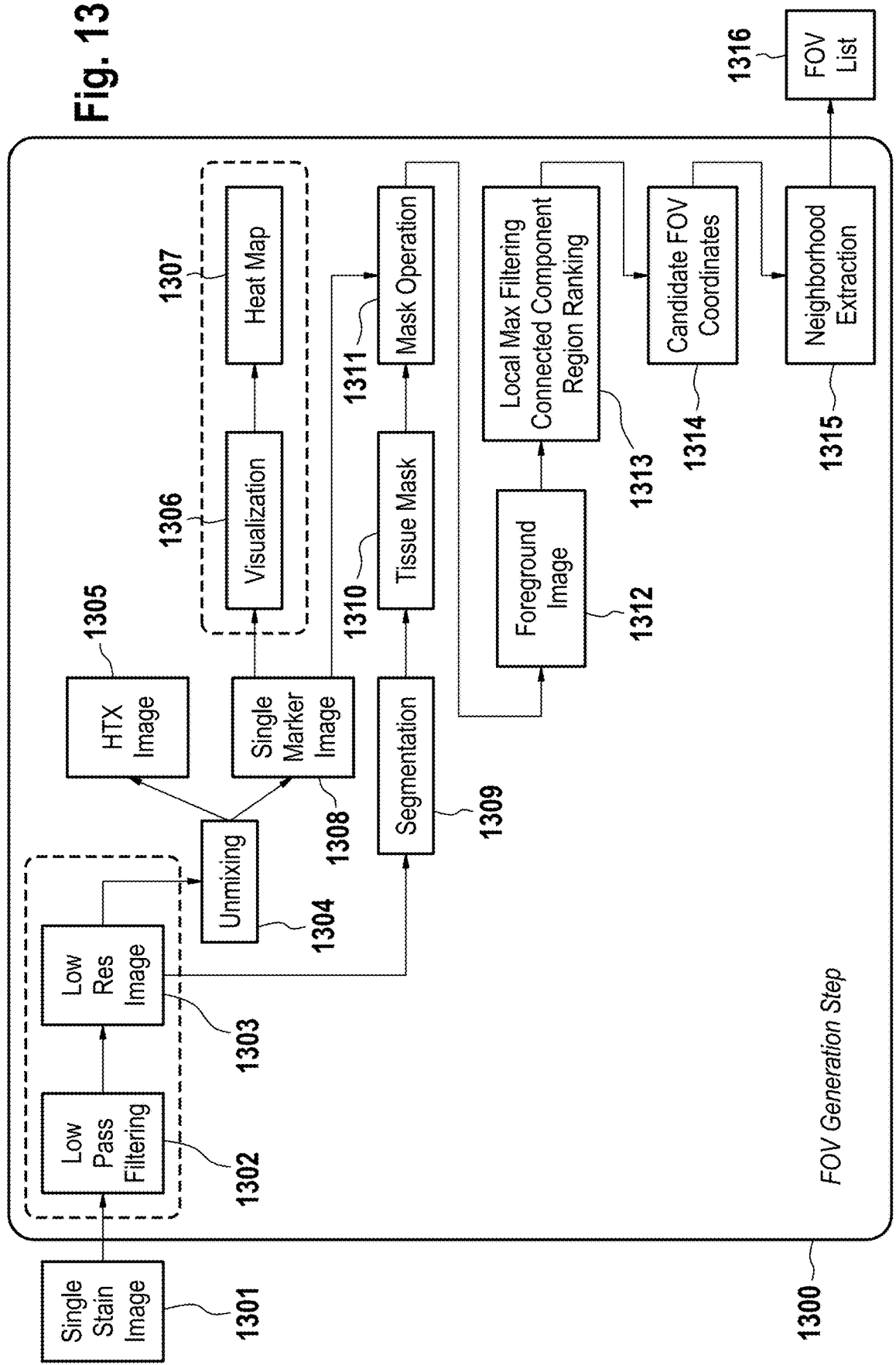
FIG. 13 depicts a process flow chart for an exemplary embodiment of the present invention starting with a single stain image.

FIG. 13 shows yet another process flow of an alternative embodiment of the present invention, using single stain images (1301) as inputs. The images are low-pass filtered (1302). In some embodiments, the images may be converted to a lower resolution (1303), which speeds processing. In some embodiments an unmixing step (1304) may be applied to extract the color channel of interest from the single stain slides, if it is not already reduced to a single color channel, producing single marker images (1308). In some embodiments an HTX image (1305) may also be generated. In other embodiments, the single marker image may be visualized (1306) using a heat map (1307), by assigning colors to regions of varying intensity in the single marker image. In one embodiment, the lower resolution images are segmented (1309) to identify features of interest. From the segmented image, a tissue region mask (1310) is generated and then the mask operation is applied (1311) to the segmented image, resulting in a foreground image (1312), which displays the intensity of the marker image only in the tissue region of interest. In another embodiment, the mask operation (1311) is applied to the single marker image (1308), resulting in a foreground image (1312). In either embodiment, the foreground image (1312) is passed through a local max filter (1313) to identify peaks in intensity. Candidate FOV coordinates are identified as the top K peaks of the local max filtered image (1314). Finally, regions around each candidate FOV coordinate are defined (1315) to obtain the list of candidate FOVs (1316). These operations are performed for each single stain slide. The FOV merging step proceeds as in FIG. 11b.

The computer-implemented method for automatic FOV selection, in accordance with the present invention, has been described, for exemplary purposes, in connection with the identification of immune cells, and for use in immunoscore computations. However, the computer-implemented method for automatic FOV selection, in accordance with the present invention, is applicable to images of any type of image of a cell or image of a biological specimen, and is applicable to determinations of type, density and location for any type of cell or group of cells. Moreover, besides medical applications such as anatomical or clinical pathology, prostrate/lung cancer diagnosis, etc., the same methods may be performed to analysis other types of samples such as remote sensing of geologic or astronomical data, etc. The operations disclosed herein may be ported into a hardware graphics processing unit (GPU), enabling a multi-threaded parallel implementation.

Figure 23:
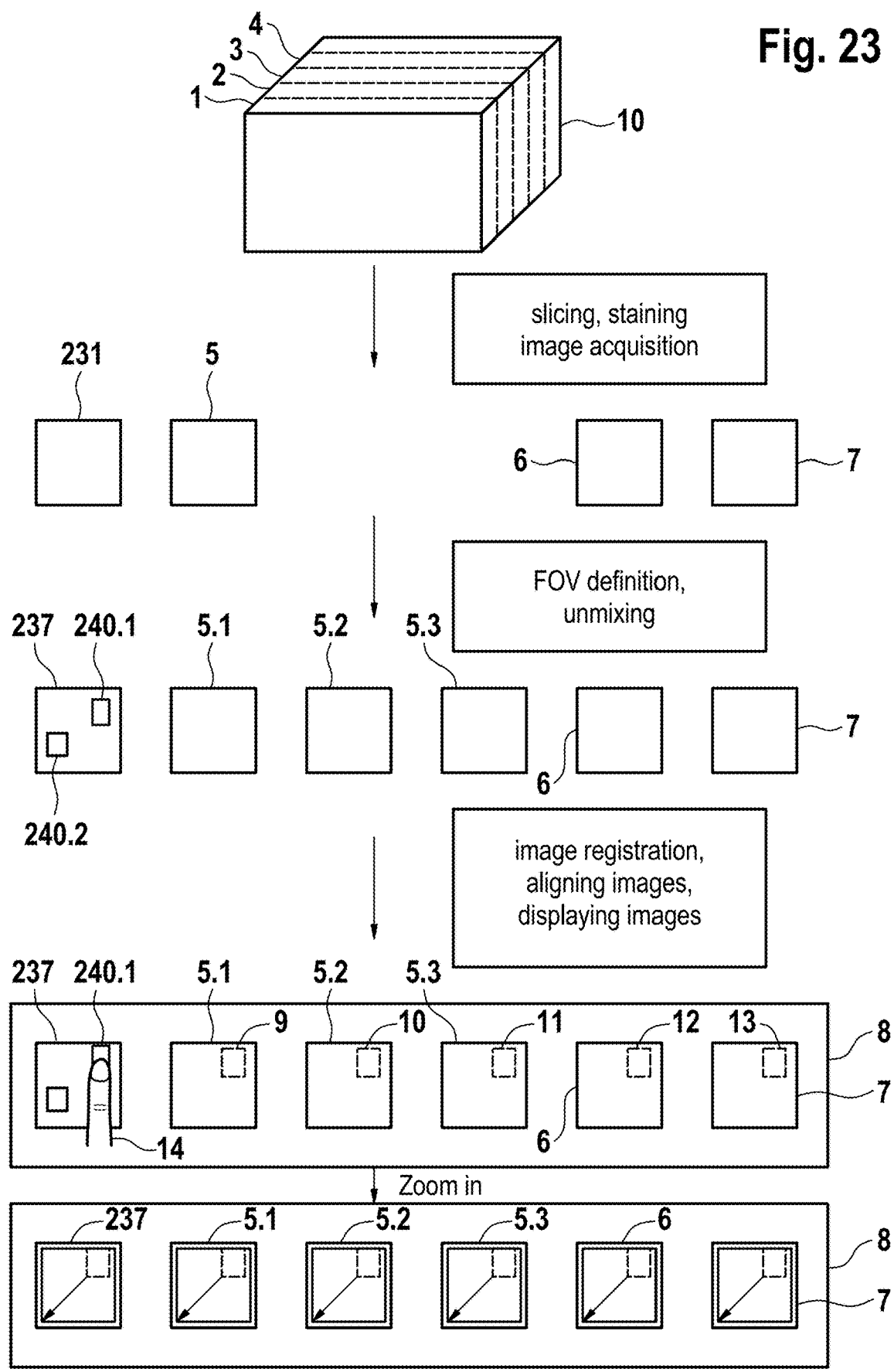
FIG. 23 depicts a schematic diagram illustrating embodiments of the present invention.

FIG. 23 shows a biopsy tissue sample 10 that has been obtained from a tissue region of a patient. The tissue sample 10 is sliced into neighboring tissue slices, such as tissue slices 1, 2, 3 and 4 as illustrated in FIG. 23. The tissue slices may have a thickness in the micrometer range, such as between 1 µm-10 µm, for example 6 µm.

The tissue slices are stained with a single stain, a stain and a counter-stain or multiple stains. This way e.g. the image 231 (cf. FIG. 2) that is stained by a stain and a counter-stain is obtained as well as a multi-channel image 5.

The multi-channel image 5 may be obtained from one of the tissue slices 1, 2, 3 and 4 that is stained by multiple stains, e.g. multiplex slide 121 of FIG. 1B that may carry one of the tissue slices. In addition further images may be acquired from the stained tissue slices such as single stain images 6 and 7. These images 231, 5, 6 and 7 may be stored in the electronic memory of an image processing system, such as in the electronic memory of a computer 101 (cf. FIG. 1A), which may be a server computer.

An automatic field of view definition may be performed with respect to one or more of the multiple images, such as with respect to the image 231 which results in the thresholded image 237 in which the fields of view 240.1 and 240.2 are indicated by respective rectangular boxes in accordance with the embodiment of FIG. 2. The image 5 is unmixed which provides a set of unmixed images 5.1, 5.2 and 5.3 assuming, without limitation of generality, that N=3 (cf. FIG. 1B). It is to be noted that the unmixed images 5.1, 5.2 and 5.3 share exactly the same coordinate system as they are all obtained from the same multi-channel image 5 such that no image registration or image alignment is required with respect to the this set of images. The additional images 6 and 7 may or may not undergo an image processing operation.

The images 231/237, 5, 6 and 7 are then registered and aligned using an image registration algorithm. For example, the multi-channel image 5 is selected as a reference image for performing the image registration algorithm. The image registration algorithm generates a geometrical transformation of each one of the other images, i.e. images 231/237, 6 and 7 with respect to the multi-channel image 5. Using the multi-channel image 5 as a reference image for the registration has the advantage that only 3 alignment operations need be executed in the example considered here. In comparison, when e.g. image 7 would have been selected as the reference image, 5 alignment operations would be required to transform the images 231/237, 5.1, 5.2, 5.3 and 6 for alignment with image 7. Hence, selecting the multi-channel image 5 as the reference substantially reduces the computational burden and reduces latency times for the image alignments.

For example, a mapping is generated for each one of the other images 231/237, 6 and 7 to the reference image 5 such as a mapping for mapping each pixel of the image 231/237 to a respective pixel in the image 5, a mapping for mapping each pixel of the image 6 to a respective pixel in the multi-channel image 5, etc. In the example considered here this results in three mappings. It is to be noted that the mapping for mapping image 231/237 to the multi-channel image 5 can be obtained using either image 231 or image 237 as these two images share the same coordinate system due to the unmixing step performed in accordance with FIG. 2.

The geometrical transformations, i.e. the mappings in the example considered here, that are obtained as a result of the image registration are then utilized to align the images 237, 6 and 7 with respect to the reference image, i.e. the multi-channel image 5/unmixed images 5.1, 5.2 and 5.3.

These aligned images are displayed on display 8 such as of computer 101 (cf. the embodiment of FIG. 1) or the display of a mobile battery-powered telecommunication device, such as a smartphone, running an Android or iOS operating system, for example. In the latter case the images 237, 5.1, 5.2, 5.3, 6, 7 and the geometrical transformations, e.g. the mappings, obtained from the image registration and meta data being indicative of the fields of view 240.1 and 240.2 are transmitted via a telecommunication network, such as a mobile cellular digital telecommunication network e.g. in accordance with the GSM, UMTS, CDMA or Long-Term Evolution standard, to the mobile battery-powered telecommunication device. The display 8 may be touch-sensitive which enables to enter commands via the graphical user interface of the computer 101 or telecommunication device by means of gesture recognition.

In one embodiment the user may select one of the fields of view by touching the respective geometrical object, i.e. a rectangular box, that symbolizes the field of view. As illustrated in FIG. 23 by way of example only this may be the field of view 240.1 on which the user places one of his or her fingers 14. In response to this gesture, a zoom in image transformation is executed by magnifying the field of view as also illustrated in FIG. 23.

An identical zoom in transformation is synchronously executed with respect to the other images 5.1, 5.2, 5.3, 6 and 7: The field of view 240.1 corresponds to image portions 9, 10, 11, 12, 13 in the images 5.1, 5.2, 5.3, 6 and 7, respectively. These image portions 9 to 13 are giving by the respective geometrical transformations obtained from the image registration, i.e. the mappings. In response to the user's gesture, i.e. touching field of view 240.1 with finger 14, the zoom in image transformation that is executed with respect to the field of view 240.1 is synchronously also executed with respect to the image portions 9 to 13.

Figure 24:
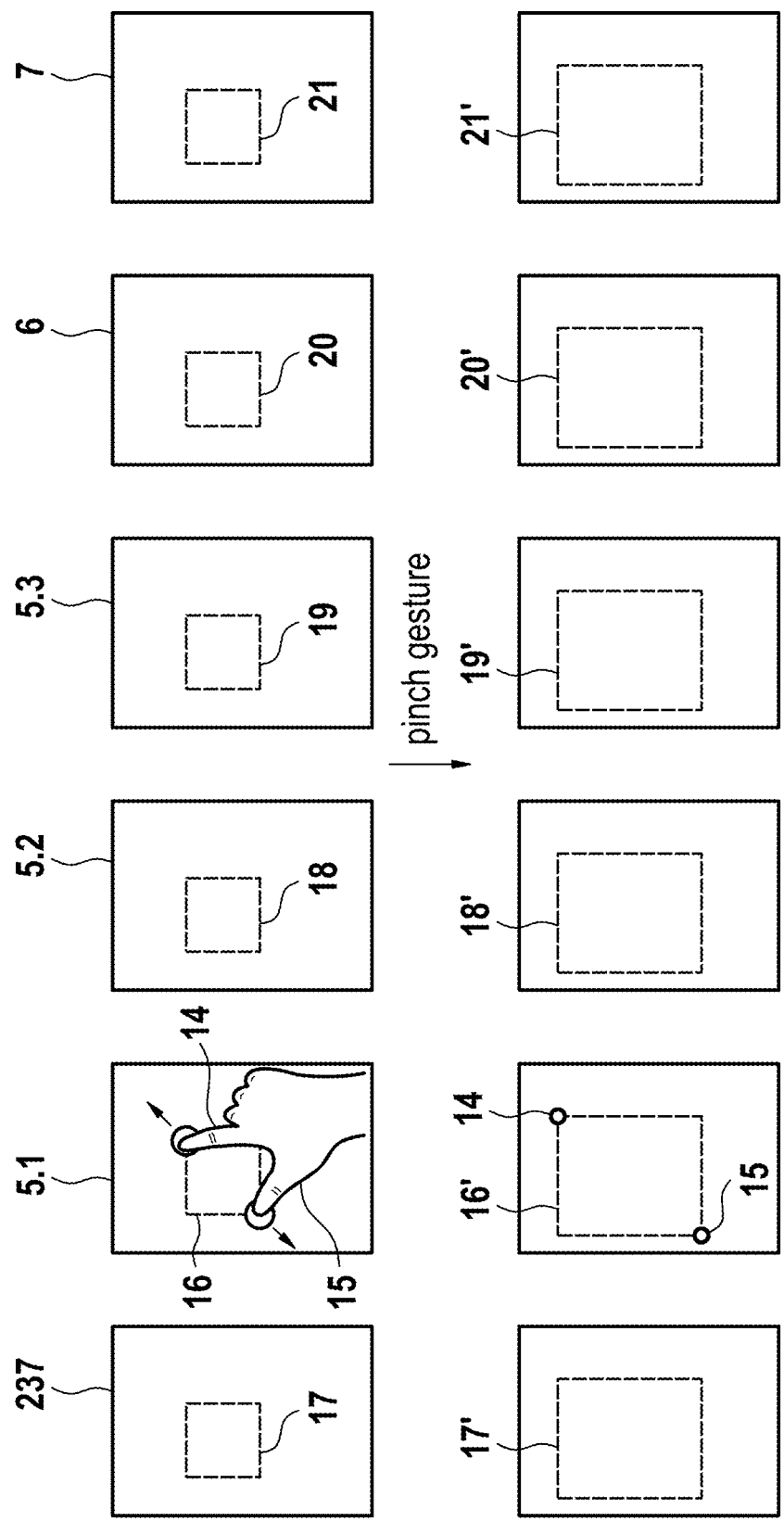
FIG. 24 illustrates an embodiment of the present invention where a pinch gesture is used to zoom in or zoom out.

FIG. 24 shows an alternative embodiment where a pinch gesture is utilized to zoom in or zoom out. The user may select a portion of one of the images, such as of image 5.1 by placing two fingers 14 and 15 on the display 8 thus defining a rectangular region 16. This rectangular region 16 corresponds to co-located image regions 17 to 21 in the other images 237, 5.2, 5.3, 6 and 7, respectively, which are given by the geometrical transformations obtained from the image registration, i.e. the mappings. Regions 18 and 19 are identical to region 16 as images 5.1, 5.2 and 5.3 share the identical coordinate system.

By distancing the fingers 15 and 14 as illustrated in FIG. 24 a zoom in is executed with respect to region 16 which provides magnified image portion 16' and synchronously also with respect to the other co-located regions 17-21, which provides the magnified regions 17', 18', 19', 20' and 21'. A zoom out can be performed analogously by reducing the distance of fingers 14 and 15.

Computers typically include known components, such as a processor, an operating system, system memory, memory storage devices, input-output controllers, input-output devices, and display devices. It will also be understood by those of ordinary skill in the relevant art that there are many possible configurations and components of a computer and may also include cache memory, a data backup unit, and many other devices. Examples of input devices include a keyboard, a cursor control devices (e.g., a mouse), a microphone, a scanner, and so forth. Examples of output devices include a display device (e.g., a monitor or projector), speakers, a printer, a network card, and so forth. Display devices may include display devices that provide visual information, this information typically may be logically and/or physically organized as an array of pixels. An interface controller may also be included that may comprise any of a variety of known or future software programs for providing input and output interfaces. For example, interfaces may include what are generally referred to as "Graphical User Interfaces" (often referred to as GUI's) that provide one or more graphical representations to a user. Interfaces are typically enabled to accept user inputs using means of selection or input known to those of ordinary skill in the related art. The interface may also be a touch screen device. In the same or alternative embodiments, applications on a computer may employ an interface that includes what are referred to as "command line interfaces" (often referred to as CLI's). CLI's typically provide a text based interaction between an application and a user. Typically, command line interfaces present output and receive input as lines of text through display devices. For example, some implementations may include what are referred to as a "shell" such as Unix Shells known to those of ordinary skill in the related art, or Microsoft Windows Powershell that employs object-oriented type programming architectures such as the Microsoft .NET framework.

Those of ordinary skill in the related art will appreciate that interfaces may include one or more GUI's, CLI's or a combination thereof. A processor may include a commercially available processor such as a Celeron, Core, or Pentium processor made by Intel Corporation, a SPARC processor made by Sun Microsystems, an Athlon, Sempron, Phenom, or Opteron processor made by AMD Corporation, or it may be one of other processors that are or will become available. Some embodiments of a processor may include what is referred to as multi-core processor and/or be enabled to employ parallel processing technology in a single or multi-core configuration. For example, a multi-core architecture typically comprises two or more processor "execution cores". In the present example, each execution core may perform as an independent processor that enables parallel execution of multiple threads. In addition, those of ordinary skill in the related will appreciate that a processor may be configured in what is generally referred to as 32 or 64 bit architectures, or other architectural configurations now known or that may be developed in the future.

A processor typically executes an operating system, which may be, for example, a Windows type operating system from the Microsoft Corporation; the Mac OS X operating system from Apple Computer Corp.; a Unix or Linux-type operating system available from many vendors or what is referred to as an open source; another or a future operating system; or some combination thereof. An operating system interfaces with firmware and hardware in a well-known manner, and facilitates the processor in coordinating and executing the functions of various computer programs that may be written in a variety of programming languages. An operating system, typically in cooperation with a processor, coordinates and executes functions of the other components of a computer. An operating system also provides scheduling, input-output control, file and data management, memory management, and communication control and related services, all in accordance with known techniques.

System memory may include any of a variety of known or future memory storage devices that can be used to store the desired information and that can be accessed by a computer. Computer readable storage media may include volatile and non-volatile, removable and non-removable media implemented in any method or technology for storage of information such as computer readable instructions, data structures, program modules, or other data. Examples include any commonly available random access memory (RAM), read-only memory (ROM), electronically erasable programmable read-only memory (EEPROM), digital versatile disks (DVD), magnetic medium, such as a resident hard disk or tape, an optical medium such as a read and write compact disc, or other memory storage device. Memory storage devices may include any of a variety of known or future devices, including a compact disk drive, a tape drive, a removable hard disk drive, USB or flash drive, or a diskette drive. Such types of memory storage devices typically read from, and/or write to, a program storage medium such as, respectively, a compact disk, magnetic tape, removable hard disk, USB or flash drive, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage device used in conjunction with memory storage device. In some embodiments, a computer program product is described comprising a computer usable medium having control logic (computer software program, including program code) stored therein. The control logic, when executed by a processor, causes the processor to perform functions described herein. In other embodiments, some functions are implemented primarily in hardware using, for example, a hardware state machine. Implementation of the hardware state machine so as to perform the functions described herein will be apparent to those skilled in the relevant arts. Input-output controllers could include any of a variety of known devices for accepting and processing information from a user, whether a human or a machine, whether local or remote. Such devices include, for example, modem cards, wireless cards, network interface cards, sound cards, or other types of controllers for any of a variety of known input devices. Output controllers could include controllers for any of a variety of known display devices for presenting information to a user, whether a human or a machine, whether local or remote. In the presently described embodiment, the functional elements of a computer communicate with each other via a system bus. Some embodiments of a computer may communicate with some functional elements using network or other types of remote communications. As will be evident to those skilled in the relevant art, an instrument control and/or a data processing application, if implemented in software, may be loaded into and executed from system memory and/or a memory storage device. All or portions of the instrument control and/or data processing applications may also reside in a read-only memory or similar device of the memory storage device, such devices not requiring that the instrument control and/or data processing applications first be loaded through input-output controllers. It will be understood by those skilled in the relevant art that the instrument control and/or data processing applications, or portions of it, may be loaded by a processor, in a known manner into system memory, or cache memory, or both, as advantageous for execution. Also, a computer may include one or more library files, experiment data files, and an internet client stored in system memory. For example, experiment data could include data related to one or more experiments or assays, such as detected signal values, or other values associated with one or more sequencing by synthesis (SBS) experiments or processes. Additionally, an internet client may include an application enabled to access a remote service on another computer using a network and may for instance comprise what are generally referred to as "Web Browsers". In the present example, some commonly employed web browsers include Microsoft Internet Explorer available from Microsoft Corporation, Mozilla Firefox from the Mozilla Corporation, Safari from Apple Computer Corp., Google Chrome from the Google Corporation, or other type of web browser currently known in the art or to be developed in the future. Also, in the same or other embodiments an Internet client may include, or could be an element of, specialized software applications enabled to access remote information via a network such as a data processing application for biological applications.

A network may include one or more of the many various types of networks well known to those of ordinary skill in the art. For example, a network may include a local or wide area network that may employ what is commonly referred to as a TCP/IP protocol suite to communicate. A network may include a network comprising a worldwide system of interconnected computer networks that is commonly referred to as the Internet, or could also include various intranet architectures. Those of ordinary skill in the related arts will also appreciate that some users in networked environments may prefer to employ what are generally referred to as "firewalls" (also sometimes referred to as Packet Filters, or Border Protection Devices) to control information traffic to and from hardware and/or software systems. For example, firewalls may comprise hardware or software elements or some combination thereof and are typically designed to enforce security policies put in place by users, such as for instance network administrators, etc.

The foregoing disclosure of the exemplary embodiments of the present subject disclosure has been presented for purposes of illustration and description. It is not intended to be exhaustive or to limit the subject disclosure to the precise forms disclosed. Many variations and modifications of the embodiments described herein will be apparent to one of ordinary skill in the art in light of the above disclosure. The scope of the subject disclosure is to be defined only by the claims appended hereto, and by their equivalents.

Further, in describing representative embodiments of the present subject disclosure, the specification may have presented the method and/or process of the present subject disclosure as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present subject disclosure should not be limited to the performance of their steps in the order written, and one skilled in the art can readily appreciate that the sequences may be varied and still remain within the spirit and scope of the present subject disclosure.

What is claimed is:

1. A system for simultaneously displaying multiple views of a same region of an object of interest, the system comprising:
   a processor; and
   a memory coupled to the processor, the memory stores computer-readable instructions that, when executed by the processor, cause the system to perform operations comprising:
      receiving a plurality of preprocessed images depicting the multiple views of the same region corresponding to at least part of the object of interest, wherein each preprocessed image is associated with (i) an image-viewing mode, and (ii) metadata that describe a preprocessed image with respect to a global-standard-reference image frame (GSRF);
      generating, using the GSRF, a common display reference frame that identifies a location, an orientation, a magnification, or combinations thereof relative to the GSRF;
      converting the plurality of preprocessed images to a set of displayable images, wherein each displayable image of the set of displayable images is generated by applying a corresponding preprocessed image of the plurality of preprocessed images to the common display reference frame to transform each pixel location of the corresponding preprocessed image to a corresponding pixel location of the displayable image, and wherein the operation of converting the plurality of preprocessed images to the set of displayable images comprises:
         constructing a copy of the common display reference frame and an affine partial mapping for the common display reference frame;
         processing the affine partial mapping with a first affine mapping of the preprocessed image to generate a composite mapping; and
         generating the displayable image of the set of displayable images, wherein the displayable image includes a set of pixels, and wherein the displayable image is generated based on operations comprising:
            for each image pixel of a set of image pixels:
               using the composite mapping to map a location of the image pixel to a corresponding location of a pixel in the preprocessed image;
               estimating a pixel value for neighboring pixels in the preprocessed image based on the corresponding location; and
               designating the estimated pixel value of the neighboring pixels as a pixel value of the image pixel;
      arranging the set of displayable images into a display pattern for viewing on a display screen; and
      causing the arranged set of displayable images to be simultaneously displayed on the display screen.

2. The system of claim 1, wherein the metadata of each preprocessed image includes a preprocessed-image local-reference image frame (PI-LRF).

3. The system of claim 2, wherein the GSRF is a fixed reference image frame that indicates spatial relationships between two or more preprocessed images of the plurality of preprocessed images by defining affine mappings between each PI-LRF and the GSRF, and wherein the metadata further includes the first affine mapping between the PI-LRF and the GSRF.

4. The system of claim 1, wherein the operations further comprise:
   receiving a user action to manipulate a displayable image of the arranged set of displayable images; and
   manipulating all other displayable images of the arranged set of displayable images in unison with the displayable image based on the user action.

5. The system of claim 1, wherein generating the common display reference frame comprises:
   creating a display image pixel grid;
   constructing a display image local reference frame (DI-LRF) that indicates pixel locations associated with the display image pixel grid, wherein the DI-LRF corresponds to the common display reference frame;
   determining a location, an orientation, and a magnification for the DI-LRF with reference to the GSRF;
   computing an affine transform that maps the pixel locations of the DI-LRF to corresponding pixel locations of the GSRF; and
   generating the affine partial mapping for the common display reference frame based on the computed affine transform.

6. The system of claim 1, wherein the object of interest is a biological tissue sample.

7. The system of claim 1, wherein the operation of converting the plurality of preprocessed images to the set of displayable images further includes performing nonlinear corrections on each preprocessed image of the plurality of preprocessed images.

8. The system of claim 1, wherein the operations further comprise: (i) increasing a magnification level of the set of displayable images in unison on the display screen in response to a user action on a displayable image, (ii) moving the set of displayable images in unison on the display screen in response to the user action on the displayable image, (iii) rotating the set of displayable images in unison on the display screen in response to the user action on the displayable image, or (iv) a combination thereof.

9. A non-transitory computer-readable medium storing instructions which, when executed by one or more processors of a system for simultaneously displaying multiple views of a same region of an object of interest, cause the system to perform a method comprising:
receiving a plurality of preprocessed images depicting the multiple views of the same region corresponding to at least part of the object of interest, wherein each preprocessed image is associated with (i) an image-viewing mode, and (ii) metadata that describe a preprocessed image with respect to a global-standard-reference image frame (GSRF);
generating, using the GSRF, a common display reference frame that identifies a location, an orientation, a magnification, or combinations thereof relative to the GSRF;
converting the plurality of preprocessed images to a set of displayable images, wherein each displayable image of the set of displayable images is generated by applying a corresponding preprocessed image of the plurality of preprocessed images to the common display reference frame to transform each pixel location of the corresponding preprocessed image to a corresponding pixel location of the displayable image, wherein converting the plurality of preprocessed images to the set of displayable images comprises:
constructing a copy of the common display reference frame and an affine partial mapping for the common display reference frame;
processing the affine partial mapping with a first affine mapping of the preprocessed image to generate a composite mapping; and
generating the displayable image of the set of displayable images, wherein the displayable image includes a set of pixels, and wherein the displayable image is generated based on operations comprising:
for each image pixel of a set of image pixels:
using the composite mapping to map a location of the image pixel to a corresponding location of a pixel in the preprocessed image;
estimating a pixel value for neighboring pixels in the preprocessed image based on the corresponding location; and
designating the estimated pixel value of the neighboring pixels as a pixel value of the image pixel;
arranging the set of displayable images into a display pattern for viewing on a display screen; and
causing the arranged set of displayable images to be simultaneously displayed on the display screen.

10. The non-transitory computer-readable medium of claim 9, wherein the metadata of each preprocessed image includes a preprocessed-image local-reference image frame (PI-LRF).

11. The non-transitory computer-readable medium of claim 10, wherein the GSRF is a fixed reference image frame that indicates spatial relationships between two or more preprocessed images of the plurality of preprocessed images by defining affine mappings between each PI-LRF and the GSRF, and wherein the metadata further includes the first affine mapping between the PI-LRF and the GSRF.

12. The non-transitory computer-readable medium of claim 9, wherein generating the common display reference frame comprises:
creating a display image pixel grid;
constructing a display image local reference frame (DI-LRF) that indicates pixel locations associated with the display image pixel grid, wherein the DI-LRF corresponds to the common display reference frame;
determining a location, an orientation, and a magnification for the DI-LRF with reference to the GSRF;
computing an affine transform that maps the pixel locations of the DI-LRF to corresponding pixel locations of the GSRF; and
generating the affine partial mapping for the common display reference frame based on the computed affine transform.

13. The non-transitory computer-readable medium of claim 9, wherein the object of interest is a biological tissue sample.

14. A computer-implemented method comprising:
receiving a plurality of preprocessed images depicting the multiple views of the same region corresponding to at least part of the object of interest, wherein each preprocessed image is associated with (i) an image-viewing mode, and (ii) metadata that describe a preprocessed image with respect to a global-standard-reference image frame (GSRF);
generating, using the GSRF, a common display reference frame that identifies a location, an orientation, a magnification, or combinations thereof relative to the GSRF;
converting the plurality of preprocessed images to a set of displayable images, wherein each displayable image of the set of displayable images is generated by applying a corresponding preprocessed image of the plurality of preprocessed images to the common display reference frame to transform each pixel location of the corresponding preprocessed image to a corresponding pixel location of the displayable image, wherein converting the plurality of preprocessed images to the set of displayable images comprises:
constructing a copy of the common display reference frame and an affine partial mapping for the common display reference frame;
processing the affine partial mapping with a first affine mapping of the preprocessed image to generate a composite mapping; and
generating the displayable image of the set of displayable images, wherein the displayable image includes a set of pixels, and wherein the displayable image is generated based on operations comprising:
for each image pixel of a set of image pixels:
using the composite mapping to map a location of the image pixel to a corresponding location of a pixel in the preprocessed image;
estimating a pixel value for neighboring pixels in the preprocessed image based on the corresponding location; and
designating the estimated pixel value of the neighboring pixels as a pixel value of the image pixel;

arranging the set of displayable images into a display pattern for viewing on a display screen; and causing the arranged set of displayable images to be simultaneously displayed on the display screen.

15. The computer-implemented method of claim 14, wherein the metadata of each preprocessed image includes a preprocessed-image local-reference image frame (PI-LRF).

16. The computer-implemented method of claim 15, wherein the GSRF is a fixed reference image frame that indicates spatial relationships between two or more preprocessed images of the plurality of preprocessed images by defining affine mappings between each PI-LRF and the GSRF, and wherein the metadata further includes the first affine mapping between the PI-LRF and the GSRF.

17. The computer-implemented method of claim 14, wherein generating the common display reference frame comprises:

creating a display image pixel grid;

constructing a display image local reference frame (DI-LRF) that indicates pixel locations associated with the display image pixel grid, wherein the DI-LRF corresponds to the common display reference frame;

determining a location, an orientation, and a magnification for the DI-LRF with reference to the GSRF;

computing an affine transform that maps the pixel locations of the DI-LRF to corresponding pixel locations of the GSRF; and generating the affine partial mapping for the common display reference frame based on the computed affine transform.

\* \* \* \* \*